(12) United States Patent
Antonsson et al.

(10) Patent No.: US 6,514,498 B1
(45) Date of Patent: *Feb. 4, 2003

(54) MODIFIED/CHIMERIC SUPERANTIGENS AND THEIR USE

(75) Inventors: Per Antonsson, Lund (SE); Per Björk, Helsingborg (SE); Mikael Dohlsten, Lund (SE); Johan Hansson, Lund (SE); Göran Forsberg, Lund (SE); Lars Abrahmsén, Bromma (SE); Terje Kalland, Arese (IT)

(73) Assignee: Pharmacia AB, Uppsala (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 29 days.

(21) Appl. No.: 08/695,692

(22) Filed: Aug. 12, 1996

(30) Foreign Application Priority Data

Mar. 19, 1996 (SE) .................................. 9601245

(51) Int. Cl.[7] .......................... A61K 39/44; A61K 39/38; A61K 39/02
(52) U.S. Cl. ................................ 424/178.1; 424/182.1; 424/184.1; 424/185.1; 424/190.1; 424/192.1; 424/194.1
(58) Field of Search ........................... 424/178.1, 182.1, 424/184.1, 185.1, 190.1, 192.1, 194.1

(56) References Cited

U.S. PATENT DOCUMENTS

| | | |
|---|---|---|
| 3,627,644 A | 12/1971 | Okamoto et al. |
| 4,237,224 A | 12/1980 | Cohen et al. |
| 4,268,434 A | 5/1981 | Higerd et al. |
| 4,681,870 A | 7/1987 | Balint, Jr. et al. |
| 4,699,783 A | 10/1987 | Terman et al. |
| 4,980,160 A | 12/1990 | Goldberg et al. |
| 5,091,091 A | 2/1992 | Terman |
| 6,126,945 A | * 10/2000 | Terman et al. |

FOREIGN PATENT DOCUMENTS

| | | |
|---|---|---|
| DE | 2828947 | 1/1979 |
| EP | 355047 | 2/1990 |

(List continued on next page.)

OTHER PUBLICATIONS

Kimmel et al (J. Neurosur., 1987, 66:161–171).*
Giantonio et al (J. Clin. Oncol., 15:1994–2007), 1994.*
Herbert et A, (The Dictionary of Immunology, Academic Press, 4th Ed, London, 1995, pp. 10&15.*

(List continued on next page.)

Primary Examiner—Susan Ungar
(74) Attorney, Agent, or Firm—Fulbright & Jaworski, L.L.P.

(57) ABSTRACT

A conjugate between a target-seeking moiety and a modified superantigen, characterized in that the superantigen is a wild-type superantigen (SA I) in which an amino acid residue in a superantigen region (region I) determining binding to TCR, referably TCRVβ, and T cell activation has been replaced by another amino acid residue while retaining the ability to activate a subset of T cells.

In a preferred embodiment the modified superantigen is a chimer between at least two wild-type superantigens (SA I, SA II etc) characterized in that one or more amino acid residues in a region determining binding to TCR and T cell activation have been interchanged between various wild-type superantigens.

A therapeutic method making use of modified/chimeric superantigens as defined in the preceding paragraphs.

An antibody preparation in which the cysteine residues that provide for interchain disulfide bonds have been mutated so as to forbid interchain disulfide bridges, preferably to serine residues, for use as a pharmaceutical.

12 Claims, 7 Drawing Sheets

FOREIGN PATENT DOCUMENTS

| WO | 8702602 | 5/1987 |
|---|---|---|
| WO | WO8907947 | 9/1989 |
| WO | 9000592 | 2/1990 |
| WO | 9100342 | 1/1991 |
| WO | WO9104053 | 4/1991 |
| WO | WO9110680 | 7/1991 |
| WO | WO9201470 | 2/1992 |
| WO | WO9301302 | 1/1993 |
| WO | WO9314634 | 8/1993 |
| WO | WO9324136 | 12/1993 |
| WO | WO9601650 | 1/1996 |

OTHER PUBLICATIONS

Todd et al., Toxic Shock Syndrome Associated with Phage–Group I Staphylococci Lancet 2: 116–120 (1978).

Shands et al., Toxic Shock Syndrome in Menstruating Woman: Association with Tampon Use and *Staphylococcus aureus* and Clinical Features in 52 Cases New Engl, J. Med. 303 1436–1441 (1980).

Fisher et al., Cardio–respiratory Failure in Toxic Shock Syndrome: Effect of Dobutamine Critical Care Medicine 13: 160–165 (1985).

Bergdoll et al., A New Staphylococcus Enterotoxin, Enter-toxin F, Associated with the Toxic Shock Syndrome *Staphylococcus aureus* Isolates Lancet 2 1017–1021 (1981).

Willoughby et al., The Toxic Shock Syndrome and Streptococcal Pyrogenic Exotoxins Ann. Int. Med. 98: 559 (1983).

Cone et al., Clinical and Bacteriological Observations of a Toxic Shock–Like Syndrome due to *Streptococcus pyrogenes* New Engl. J. Med. 317: 146–148 (1987).

Stevens et al., Severe Group A Streptococcal Infections Associated with a Toxic Shock–like Syndrome and Scarlet Fever Toxin A New Engl J. Med 32: 321: 1–7 (1989).

Schilievert, PM Staphylococcal Enterotoxin B and Toxic Shock Syndrome Toxin–1 are Significantly Associated with Non–Menstrual TSS Lancet 1: 1149–1150 (1986).

Johnson et al., Mol. Gen. Genet. 203, 354 to 356 (1986).

Borja et al., Biochemistry vol. 6, No. 5, pp. 1467 to1473, 1967.

Elsberry et al., Hemodynamics of Staphylococcal B Enterotoxaemia and Other Types of Shock in Monkeys J. Applied Physiology 27 164–169.

Liu et al., Cardiovascular and Vomiting Responses to a Lethal Intravenous Dose of Staphyloenterotoxin A in Rhesus Monkeys J Med Primatol. 5:353–359 (1976).

Eur. J. Immunogenetics 19: 181–285 (1992).

Acolla RJ et al., J. Exp. Med. 157: 1053–1058 (1983).

Kravath et al., Gamma Ray–induced Loss of Expression of HLA and Glyoxalase I Alleles in Lymphoblastoid Cells Proc. Natl. Acad. Sci. USA 77: 4251–4255 (1980).

Acolla et al., J. Exp. Med. 162: 1117–1133 (1985).

Acolla et al., J. Exp. Med. 164: 369–374 (1986).

Acolla et al., Proc. Natl. Acad. Sci. USA 82: 5145–5149 (1985).

Shoemaker et al., Development of Human Tumour Cell Line Panels for use in Disease–Oriented Drug Screening in T. Hall editor Prediction of Response to Cancer Therapy Alan Liss N.Y. pp. 265–286 (1988).

Paull K.D. et al., J. Natl. Cancer Inst. 81: 1088–1092 (1989).

Alley M.C. et al., Cancer Res. 48: 589–601 (1988).

Scudiero D.A. et al., Cancer Res. 48: 4827–4833 (1988).

Developmental Therapeutics Program Division of Cancer Treatment, National Cancer Institute Proceedings of Workshop on "Selection, Characterisation and Quality Control of Human Tumour Cell Lines from the NCI's New Drug Screening Program" Bethesda, MD May 27–28, 1–73 (1987).

Boyd M.R. Status of NCI preclinical antitumour drug discovery screen in DeVita V.T., Hellman S., Rosenberg S.A., eds Cancer: Principles and Practice of Oncology Updates, vol. 3, No. 10, Lippincott, Philadelphia 1–12 (1989).

Rooney C., et al., J. Natl. Cancer Inst. (1986).

Sausville E.A. in Anticancer Drug Development Guide: Preclinical Screening, Clinical Trials and Approval B. Teicher editor, Human Press, Totowa, N.J.

D. Terman et al., "Preliminary Observations of the Effects on Breast Adenocarcinoma of Plasma Perfused Over Immobilized Protein A," New Eng. J. Med., 305:1195–1200 (1981).

F. Chu et al., "Purification and Characterization of Staphylococcal Enterotoxin A," Biochem., 5:3281 (1966).

M. Bergdoll et al., "Identification of a New Enterotoxin as Enterotoxin C," J. Bacteriol., 90:1481 (1965).

C. Borja and M. Bergdoll, "Purification and Partial Characterization of Enterotoxin C Produced by *Staphylococcus aureus* Strain 137," Biochem., 6:1467 (1967).

R. Avena and M. Bergdoll, "Purification and Some Physicochemical Properties of Enterotoxin C, *Staphylococcus aureus* Strain 361," Biochem., 6:1474 (1967).

E. Schantz et al., "Purification and Some Chemical and Physical Properties of Staphylococcal Enterotoxin A." Biochem., 11:360 (1972).

E Schantz et al., "Purification of Staphylococcal Enterotoxin B," Biochem., 4:1011 (1965).

H–C. Chang and M. Bergdoll, "Purification and Some Physicochemical Properties of Staphylococcal Enterotoxin D," Biochem., 18:1937 (1979).

C. Borja et al., "Purification and Some Physicochemical Properties of Staphylococcal Enterotoxin E," J. Biol. Chem., 247:2456 (1972).

M. Dayhoff (ed.), Data Section, in *Atlas of Protein Sequence Structure* 5:D227, National Biomedical Research Foundation, Washington, D.C. (1972).

I. Huang and M. Bergdoll, "The Primary Structure of Staphylococcal Enterotoxin B," J. Biol. Chem., 245:3493 (1970).

M. Bergdoll et al., "Enterotoxin Synthesis by the Staphylococci," In *Recent Advances in Staphylococcal Research* (W.W. Yotis, ed.), Ann. N.Y. Acad. Sci., 236:307.

J. Iandolo, "Genetic Analysis of Extracellular Toxins of *Staphylococcus aureus*," Ann. Rev. Microbiol., 43:375 (1989).

M. Bergdoll et al., "Staphylococcal Enterotoxin B, III. The Physicochemical Properties and the N—and C–Terminal Amino Acid Sequences," Arch. Biochem. Biophys., 112:104 (1965).

I. Huang et al., "Amino Acid Composition and Terminal Amino Acids of Staphylococcal Enterotoxin C," Biochem., 6:1480 (1967).

M. Bergdoll et al., "Chemistry of the Staphylococcal Enterotoxins," J. Agric. Food Chem., 22:9 (1974).

D. Blomster–Hautamaa et al., "Preparation of Toxic Shock Syndrome Toxin–1," Methods in Enzymology 165:37 (1988).

M. Bergdoll et al., "Identification of Enterotoxin E," Infect. Immun., 4:593 (1971).

M. Bergdoll, "Entertoxins," in *Staphylococci and Staphylococci Infections* (C.S.F. Easmon and C. Adlam, eds.), pp. 559–598 (1983).

J. Freer and J. Arbuthnott, "Toxins of *Staphylococcus aureus*," Pharmac. Ther., 19:55 (1983).

L. Johnson et al., "Streptococcal Pyrogenic Exotoxin Type A (scarlet fever toxin) is related to *Staphylococcus aureus* Enterotoxin B," Mol. Gen. Genet., 203:354 (1986).

W. Pearson and D. Lipman, "Improved Tools for Biological Sequence Comparison," Proc. Nat'l. Acad. Sci. USA, 85:2444 (1988).

J. Lipman and W. Pearson, "Rapid and Sensitive Protein Similarity Searches," Sci., 227:1435 (1985).

C. Janeway, Jr. et al., "T–Cell Responses to Mls and to Bacterial Proteins that Mimic its Behavior," Immunol. Rev., 107:61–88.

J. Yagi et al., "Bacterial Proteins That Mediate the Association of a Defined Subset of T Cell Receptor:CD4 Complexes With Class II MHC,"J. Immunol., 144:892–901.

H. Stewart et al., *in Atlas of Tumor Pathology*, Armed Forces Institute of Pathology, Washington, D.C., pp. 38, 355 (1959).

J. Kidd et al., "A Transplantable Rabbit Carcinoma Originating in a Virus–Induced Papilloma and Containing the Virus in Masked or Altered Form," J. Exp. Med., 71:813–838 (1940).

T. Maniatis et al., *Molecular Cloning: A Laboratory Manual*, Cold Spring Harbor Laboratory, New York (1982).

J. Betley and J. Mekalanos, "Nucleotide Sequence of the Type A Staphylococcal Enterotoxin Gene," J. Bacteriol., 170:34 (1987).

I. Huang et al., "Complete Amino Acid Sequence of Staphylococcal Enterotoxin A," J. Biol. Chem., 262:7006 (1987).

M. Betley et al., "Staphylococcal Entertoxin A Gene is Associated With a Variable Genetic Element," Proc. Natl. Acad. Sci. USA 81:5179 (1984).

M. Gaskill and S. Khan, "Regulation of the Enterotoxin B Gene in *Staphylococcus aureus*," J. Biol. Chem., 263:6276.

C. Jones and S. Khan, "Nucleotide Sequence of the Enterotoxin B Gene from *Staphylococcus aureus*," J. Bacteriol., 166:29 (1986).

I. Huang and M. Bergdoll, "The Primary Structure of Staphylococcal Enterotoxin B," J. Biol. Chem., 245:3518 (1970).

G. Bohach and P. Schlievert, "Expression of Staphylococcal Enterotoxin $C_1$ in *Escherichia coli*," Infect. Immun., 55:428 (1987).

G. Bohach and P. Schlievert, "Nucleotide Sequence of the Staphylococcal Enterotoxin $C_1$ Gene and Relatedness to Other Pyrogenic Toxins," Mol. Gen. Genet., 209:15 (1987).

J. Couch et al., "Cloning and Nucleotide Sequence of the Type E Staphylococcal Entertoxin Gene," J. Bacteriol., 170:2954 (1988).

B. Krieswirth et al., "The Toxic Shock Syndrome Exotoxin Structural Gene is Not Detectably Transmitted by a Prophage," Nature 305:709 (1983).

J. Cooney et al., "Molecular Cloning and Genetic Analysis of the Determinant for Gamma–Lysin, a Two–component Toxin of *Staphylococcus aureus*," J. Gen. Microbiol., 134:2179 (1988).

M. Friedman et al., "Induction of Mutants of *Staphylococcus aureus* 100 With Increased Ability to Product Enterotoxin A," J. Bacteriol., 106:289 (1971).

D. Terman, "Staphylococcal Protein A in Neoplastic Disease," J. Biol. Response Modifiers 3:316 (1984).

D. Terman and J. Bertram., "Antitumor Effects of Immobilized Protein A and Staphylococcal Products: Linkage Between Toxicity and Efficacy, and Identification of Potential Tumoricidal Reagent," Eur. J. Cancer Clin. Oncol., 21:1115 (1985).

D. Terman, "Immunoadsorbents in Autoimmune and Neoplastic Diseases," Plasma Ther. Transfus. Technol., 4:415 (1983).

D. Terman, "Protein A and Staphylococcal Products in Neoplastic Disease," CRC Crit. Rev. Oncol./Hematol., 4:103 (1985).

D. Terman, "Immunobilized Enzymes and Cells," *in Methods in Enzymology*, vol. 137 (K. Mosbach, ed.), Academic Press, San Diego, pp. 496–515 (1988).

J. Mikolàšek, "Direct Evidence for Rejection of Tumour Allografts in *S. pyogenes* Toxins–Treated Mice Correlated with Antistreptolysin O Level in Serum," Neoplasma 19:507 (1972).

O. Shcheglovitova et al., Eksp Onkol., 9(1):28–30 (1987), cited in: Biol. Abstr., 84(5):AB–685, Ref. 48345 (1987); O.N. Shcheglovitova et al., Eksp Onkol., 11(2):54–57 (1989), cited in: Biol. Abstr., 88(8):AB–700, Ref. 87362 (1989); and O.N. Shcheglovitova et al., Eksp Onkol., 11(1):73–74 (1989), cited in: Biol. Abstr., 88(7):AB–639, Ref. 75810 (1989).

P. Garcia Peñarrubia et al., "Selective Proliferation of Natural Killer Cells Among Monocyte–Depleted Peripheral Blood Mononuclear Cells as a Result of Stimulation with Staphylococcal Enterotoxin B," Infect. and Immun., 57:2057 (1989).

E. Carswell et al., "An Endotoxin–induced Serum Factor That Causes Necrosis of Tumors," Proc. Nat. Acad. Sci. USA 72:3666 (1975).

D. Fast et al., "Toxic Shock Syndrome–Associated Staphylococcal and Pyrogenic Toxins Are Potent Inducers of Tumor Necrosis Factor Production," Infect. Immun., 57:291 (1989).

C. Platsoucas et al., "Immunomodulation of Human Leukocytes by Staphylococcal Enterotoxin A: Augmentation of Natural Killer Cells and Induction of Suppressor Cells," Cellular Immunol., 97:371 (1986).

K. Newell et al., "In vivo T–cell Activation by Staphylococcal Enterotoxin B Prevents Outgrowth of a Malignant Tumor," Proc. Natl. Acad. Sci. USA 88:1074 (1991).

J. Kappler et al., "Vβ–Specific Stimulation of Human T Cells by Staphylococcal Toxins," Science 244:811–813 (1989).

H. Schrezenmeier and B. Fleischer, "Mitogenic Activity of Staphylococcal Protein A is Due to Contaminating Staphylococcal Enterotoxins,"J. Immun. Meth., 105:133 (1987).

J. Sjöquist et al., "Protein A Isolated From *Staphylococcus aureus* After Digestion With Lysostaphin," Eur. J. Biochem., 29:572 (1972).

J. Balint, Jr. et al., "Detection, Isolation and Characterization of Staphylococcal Enterotoxin B in Protein A Preparations Purified by Immunoglobulin G Affinity Chromotagraphy," J. Immun. Meth., 116:37 (1989).

Bowie et al (Science, 257:1306–1310), 1990.*

Burgess et al (J. Cell Biol., 111:2129–2138), 1990.*

Lazar et al (Mol Cell Biol., 8:1247–1252), 1988.*

R. Katherine Alpaugh et al., Superantigen–targeted Therapy: Phase I Escalating Repeat Dose Trial of the Fusion Protein PNU–214565 in Patients with Advanced Gastrointestinal Malignancies, Aug. 1998, vol. 4, pp. 1903–1914.
Kimmel et al (J. Neurosurg, 66:161–171), 1987.*
Herbert et al (The Dictionary of Immunology, Academic Press Inc., san Diego, p. 61 and Fig 12, p. 83), 1995.*
Abrahmsen L. et al., (1995), A. EMBO J. 14:2978–86.
Dohlsten et al., (1988), Eur J. Immunol. 18:1173–1178.
Dohlsten M. et al., (1991), Proc. Natl. Acad. Sci. USA, 88:9287–91.
Dohlsten M. et al., (1994), Proc. Natl. Acad. Sci. USA, 91:8945–49.
Fleury S. et al., (1991), Cell, 66:1037–49.
Fraser J.D. et al., (1993), In: Huber, BT Palmer, E (eds) Current Communications in Cell and Molecular Biology 7. Cold Spring Harbour Laboratory Press, Cold Spring Harbor, NY. pp. 7–29.
Grossman et al., (1991), J. Immunol. 147:3274–81.
Hartwig UF et al., (1993), Int. Immunol. 5 (8) 869–875.
Holzer U et al., (1995), Cancer Immunol. Immunother. 41(2):126–136.
Horton RM et al., (1990), Biotechniques 8:528–35.
Hudson et al., (1993), J. Exp. Med. 177:175–84.
Hufnagle WO et al., (1991), Infect. Immun. 59:2126–34.
Irwin MJ et al., (1992), Nature 359:841–3.
Kappler JW et al., (1992), J. Exp. Med. 175:387–96.
Kotzin BL et al., (1993), Adv. Immunol. 54:99–166.
Kraulis PJ, (1991), J. Appl. Cryst. 24:946–50.
Lamphear JG et al., (1996) J. Immunol. 156:2178–2185.
Lando PA et al., (1993), Immunology 80:236–241.
Mollick JA et al., (1993), J. Exp. Med. 177:283–93.
Newall et al., (1991), *Proc. Natl. Acad. Sci. USA* 88:1074–1078.
Schad EM et al., (1995), A. EMBO J. 14:3292–301.
von Heijne, G., (1986), Nucleic Acid Res., 14:1483–90.

* cited by examiner

MODIFIED/CHIMERIC SUPERANTIGENS AND THEIR USE

This application claims priority from Swedish Patent Application No 9601245-5, which was filed Mar. 29, 1996, and is incorporated herein by reference.

FIELD OF THE INVENTION

The present invention relates to functionally active modified superantigens which are wild-type superantigens (SA I) in which one or more amino acid residues have been substituted while maintaining superantigen function. In case one or more of the substituting residues (or a conserved amino acid residue thereof) occur in the corresponding positions in another wild-type superantigen (SA II), the modified superantigen is called a chimera. Chimeric superantigens thus will contain part sequences/regions deriving from at least two different wild-type superantigens.

By the term "corresponding" is meant that residues, part sequences and regions replacing each other have functionally the same position in superantigens I and II so that substitution will lead to a chimeric form that is able to function as a superantigen.

The terminology grafted/grafting/graft is used in connection with parts of the full sequence of superantigen II that have replaced corresponding parts of superantigen I, even if only one single amino acid has been replaced.

Modified/chimeric superantigens also encompass functional superantigens modified in other ways, for instance conjugated to a target-seeking moiety, including also fused forms when the moiety is a polypeptide/protein. See below.

Superantigens

According to the very first definition (around 1988–1993), superantigens are bacterial or viral proteins capable of binding to MHC class II antigens without prior intracellular processing and activate T cells by binding to the β-chain variable region (V β) of the T cell receptor (TCR). The binding leads to a Vβ family restricted activation of a relatively large proportion/subset of T cells and lysis of MHC Class II expressing cells (superantigen dependent cell cytolysis=SDCC).

Well known wild-type superantigens according to the definition above are the staphylococcal enterotoxins (SEA, SEB, SEC1, SEC2, SED, SEE and SEH). Further examples are Toxic Shock Syndrome Toxin 1 (TSST-1, also of staphylococcal origin), Exfoliating Toxins (EXft), Streptococcal Pyrogenic Exotoxin A, B and C (SPE A, B and C), Mouse Mammary Tumor Virus proteins (MMTV), Streptococcal M proteins, Clostridial Perfringens Enterotoxin (CPET), mycoplasma arthritis superantigens etc. For a review of superantigens and their properties see Kotzin et al 1993.

During the early nineties it was discovered that activation and subsequent cell lysis could occur in a MHC class II independent manner in case the superantigen was conjugated with a target-seeking moiety capable of binding to a cell surface structure (Dohlsten et al WO9201470 and Abrahmsén et al WO9601650). Upon incubation of target cells (carrying the target structure for the target-seeking moiety) and effector cells (T cells) with the conjugates, the target cells become lysed (superantigen antibody dependent cell cytolysis=SADCC) without any requirement for class II expression. Accordingly the superantigen concept of today and used in the context of the present invention, if not otherwise specified, encompasses any compound (preferably of polypeptide structure) that is capable of binding to a cell surface structure (target structure) and to one or more polymorphic TCR chain, in particular the Vβ chain, thereby activating a subset of T cells expressing the specific TCR chain involved in the binding. The T cells then become cytotoxic for cells carrying the surface structure (target structure, target cells). Normally the activated subset of T cells constitutes about 1–20% of the total amount of T cells of an individual.

Background Art—Structural and Functional Studies Utilizing Mutated and Chimeric Superantigens Chimeric superantigens including point mutated forms have previously been described (Kappler et al WO 9314364, Kappler et al 1992; Grossman et al 1991; Hufnagle et al 1991; Hartwig et al 1993; Fraser et al 1993; Mollick et al 1993; Erwin et al 1992; and Hudson et al 1993). Mollick et al and Hudson et al show from studies of chimeras that the Vβ specificity of SEA and SEE resides in certain amino acid sequences present in the carboxy terminal region (i.e. amino acid residues 200, 206 and 207). In addition to the Vβ specificity, mainly depending on this region, Mollik et al also were able to show that for complete reconstitution of SEE like activity of SEA containing SEE grafts towards Vβ8, a fragment containing the N-terminal 70 amino acid residues from SEE was needed. This fragment contains parts of the SEE-like MHC class II α chain binding site and chimeric SEA/SEE molecules containing this part from SEE, inhibited binding of SEA to MHC class II DR1 in a SEE-like manner.

Recently SEE-SEA chimers involving an exchange of regions involved in binding to TCRVβ have been described (Lamphaer et al., J. Immunol. 156 (Mar. 15, 1996) 2178–2185). A SEE superantigen Fab antibody fusion protein in which the SEE domains involved in the interaction with T cells have been replaced with the corresponding non-homologous SEA domains has been discussed at ABRF'96: Biomolecular Techniques, Holiday Inn Golden Gateway, San Francisco, Calif. Mar. 30–Apr. 2, 1996 (Björk et al., M45).

Background Art—Therapeutic Use of Superantigens

Non-conjugated superantigens have been suggested for therapy with curative effect presumably being accomplished through a general activation of the immune system (Kalland et al WO91404053; Terman et al WO9110680 and WO9324136; Newall et al 1991).

It has also been suggested to use modified superantigens conjugated to target-seeking moieties (Dohlsten et al WO9201470; Abrahmsén et al WO9601650, both hereby being incorporated by reference). This enabled a broader therapeutic use of T cell activation through Vβ. The conjugates studied so far have had a diminished class II affinity, which in turn has lead to a decrease of the severe systemic toxicity normally associated with the wild-type superantigens.

Terman et al (WO9110680; WO9324136) in side-sentences suggested cancer therapy with modified superantigens and superantigen fragments.

Kappler et al (WO9314634) have suggested to use non-conjugated to superantigens mutated to have lost their Vβ-binding ability (in the context of vaccines). Abrahmsén et al (WO9601650) have suggested cancer therapy with conjugated superantigens having a modified, preferably decreased, ability to bind to Class II antigens. The modifications encompassed single mutations as well as construction of chimeras between different superantigens.

The Problems that Have Been the Objective to Solve with the Present Invention

The sera of human populations normally contain high titers of antibodies against superantigens. For the staphylococcal superantigens, for instance, the relative titers are TSST-1>SEB>SEC1>SE3>SEC2>SEA>SED>SEE. These relative titers indicate immunogenicity problems and problems with neutralizing antibodies in case SEs are administered parenterally. Based solely on these problems, SEE should be the preferred staphylococcal superantigen. In the context of work with fusion proteins, however, we have found that the ability for T cell MHC class II independent cytotoxicity, superantigen-antibody dependent cell cytotoxicity (SADCC), of SEE conjugates is poor. The anti-SE titers also indicate that there might be advantages in modifying a "high titer" superantigen to be more like a "low titer" superantigen.

The Objectives of the Present Invention

A first objective is to improve the previously known superantigens with respect to lowering their immunogenicity and reaction with neutralizing antibodies.

A second objective is to provide superantigens with less side effects when used as a drug.

A third objective is to provide improved superantigens that can be used as the active principle in the treatment of mammals suffering from cancers, autoimmune diseases, parasitic infestations, viral infections or other diseases associated with cells that on their surface express MHC class II antigens and/or structures that are specific for respective disease and bind to a target-seeking moiety incorporated into the superantigen.

The Discovery that has Resulted in the Invention

A sequence homology analyzis of SEA and SEE (FIG. 2) reveals that the non-identical amino acid residues are concentrated to as eight distinct regions. These regions are identified by A, B, C, D, E, F, G, and H as depicted in FIG. 2. For SEA, and SEE the sequences in these regions are identified as follows:

| Region. | SEQ ID NO. for SEA | SEQ ID NO. for SEE |
|---------|-------------------|-------------------|
| A | SEQ ID NO.:9 | SEQ ID NO.:10 |
| B | SEQ ID NO.:11 | SEQ ID NO.:12 |
| C | SEQ ID NO.:13 | SEQ ID NO.:14 |
| D | SEQ ID NO.:15 | SEQ ID NO.:16 |
| E | SEQ ID NO.:17 | SEQ ID NO.:18 |
| F | SEQ ID NO.:19 | SEQ ID NO.:20 |
| G | SEQ ID NO.:21 | SEQ ID NO.:22 |
| H | SEQ ID NO.:23 | SEQ ID NO.:24 |

Outside these eight regions, making up to 34% of the sequence, the identity of the two SEs is 97%, with conserved amino acid substitutions accounting for the remaining differences. Four of these regions are structurally close to the two MHC class II binding sites (B: AA 37–50 (Sequence ID Nos. 11 and 12), D: 71–78 (Sequence ID Nos. 15 and 16), E: 136–149 (Sequence ID Nos. 17 and 18), and G 189–195 (Sequence ID Nos. 21 and 22)), and are not likely to interact with the TCR. The additional four regions (A: AA 20–27 (Sequence ID Nos. 9 and 10), C: 60–62 (Sequence ID Nos. 13 and 14), F: 161–176 (Sequence ID Nos. 19 and 20) and H:200–207(Sequence ID Nos. 23 and 24) are located on the edge of the molecule, in the vicinity of the putative TCR binding site, postulated to reside in the groove between the two subdomains. By grafting the individual regions (replacement of amino acid residues that differ), we have now found that the property of SEA-conjugates to induce a cytoxic response as well as potentiating proliferative response in the absence of MHC class II, resides in one region in the TCR binding domain of SEA. This Region (A) is transferable to SEE and has a great impact on activity in the absence of Class II, although limited effects on the Vβ specificity of the superantigen (FIG. 6, Tab.2). All of the regions (A, C, F and H) seem to participate, directly or indirectly, in the interaction with the TCR manifested by an altered stimulatory effect on murine T-cell hybridomas (Tab. 2)

Due to the analogous mode of action it is conceivable that a similar structural separation of these TCRVβ binding properties is at hand also for superantigens analogous to SEA and SEE. The same may also apply within other types of superantigens, in which the binding structures are organised differently. Our discovery has enabled us to outline the construction of chimeric superantigens that potentially are of extremely great value as therapeutic agents.

BRIEF DESCRIPTION OF THE DRAWINGS

FIGS. 1A and 1B show Superantigen dependent cellular cytotoxicity (SDCC) and FIGS. 1C and 1D show Superantigen antibody cellular cytotoxicity (SADCC) with C215Fab-SEA and C215Fab-SEE as effector molecules. Cytotoxicity was analyzed in $^{51}Cr$ release assay using a SEE-reactive human T-cell line FIG. 1A and FIG. 1C a Raji cell line as target and a SEA-reactive human T-cell line FIG. 1A and FIG. 1B. Target cell lines were Raji FIG. 1A and FIG. 1B and Colo 205 FIG. 1C and FIG. 1D.

Table 1. Purified human T-cells were stimulated for 96 h with respective C215Fab-SE presented on MHC class II negative CHO-CD80/C215 transfectants. After 72 h the cells were pulsed with $^3H$-thymidine for 24 h and incorporated label was measured and represented as half maximal concentration ($EC_{50}$).

Table 2. Murine T cell hybridomas were stimulated for 48 h with native or chimeric Fab conjugated superantigen. Activity was measured as IL-2 production and represented as half maximal concentration ($EC_{50}$).

Figure 5:
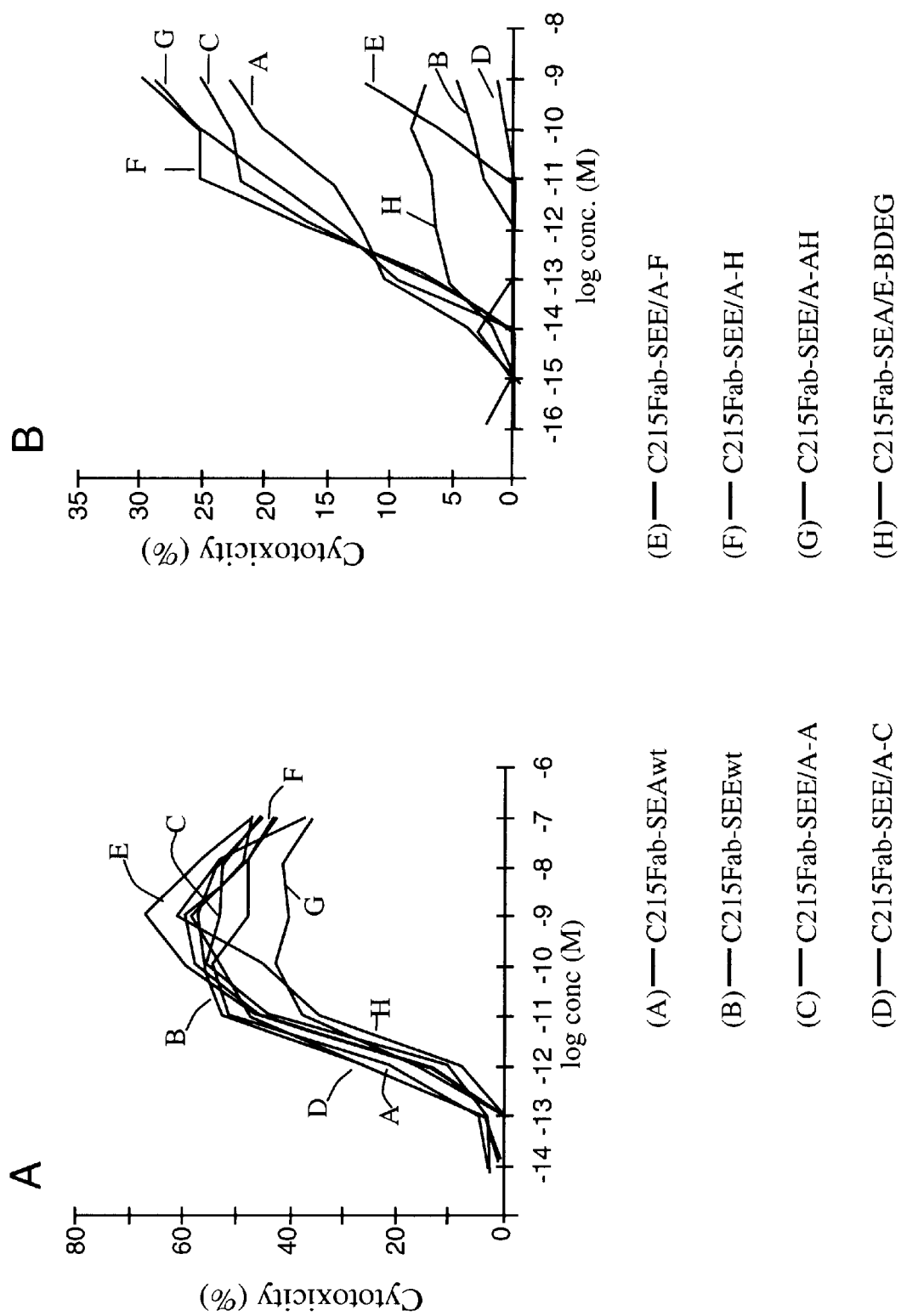

FIG. 5. FIG. 5A shows Superantigen dependent cellular cytotoxicity (SDCC) and FIG. 5B shows Superantigen antibody cellular cytotoxicity (SADCC) of C215Fab-SEE/A-A, C215Fab-SEE/A-C, C215Fab-SEE/A-F, C215Fab-SEE/A-H, C215Fab-SEE/A-AH and C215Fab-SEA/E-BDEG. Cytotoxicity was analyzed in a 51Cr release assay using a SEA-reactive human T-cell line and Raji FIG. 5A or Colo 205 FIG. 5B cell lines as targets.

Figure 6:
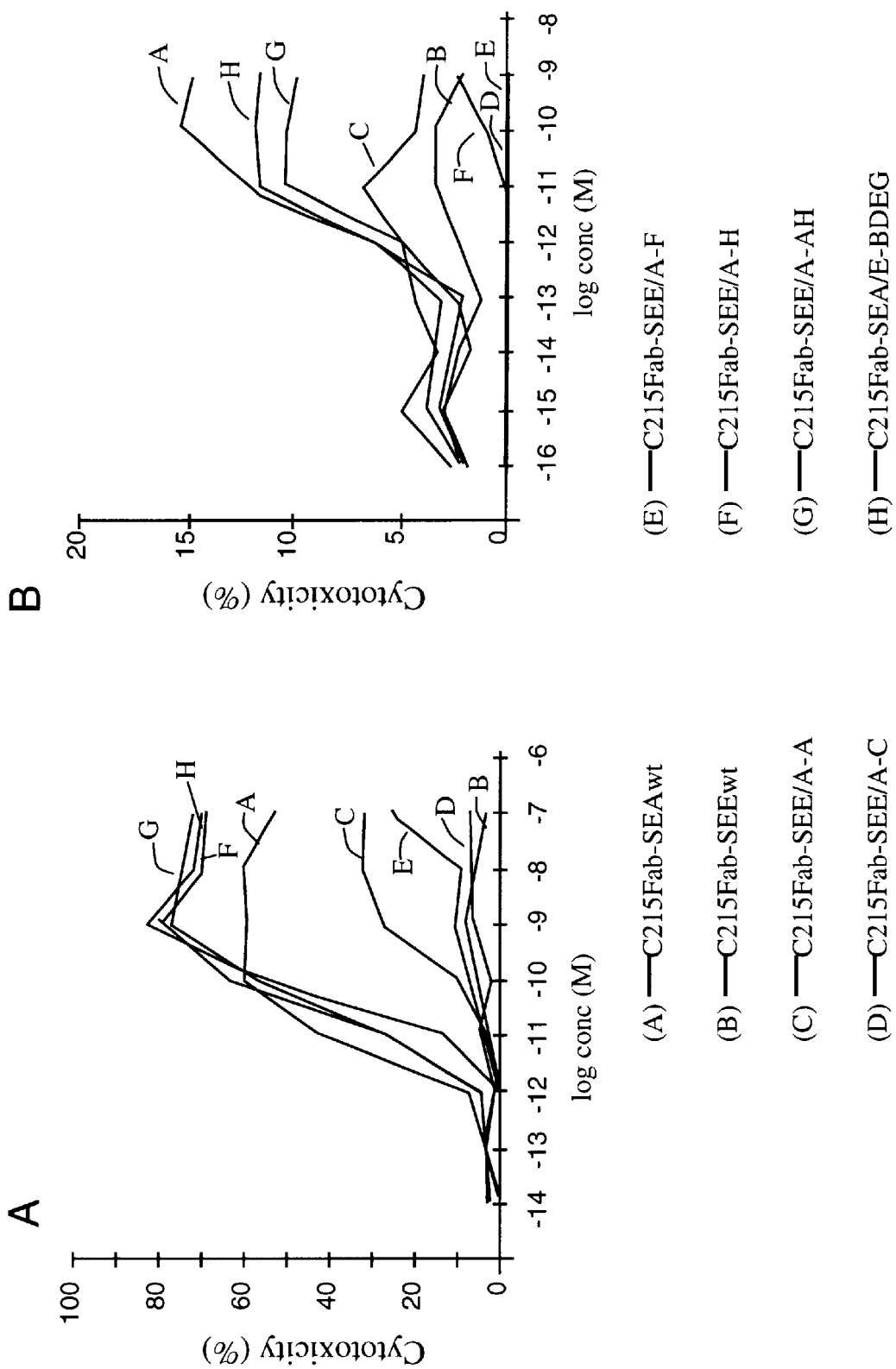

FIG. 6. FIG. 6A shows Superantigen dependent cellular cytotoxicity (SDCC) and FIG. 6B shows Superantigen antibody cellular cytotoxicity (SADCC) with C215Fab-SEA, C215Fab-SEE, C215Fab-SEE/A-A, C215Fab-SEE/A-C, C215Fab-SEE/A-F, C215Fab-SEE/A-H, C215Fab-SEE/A-AH and C215Fab-SEA/E-BDEG as effector molecules. Cytotoxicity was analyzed in a 51Cr release assay using a Vβ22 selected SEA-reactive human T-cell line and Raji FIG. 6A or Colo 205 FIG. 6B cell lines as targets.

Figure 7:
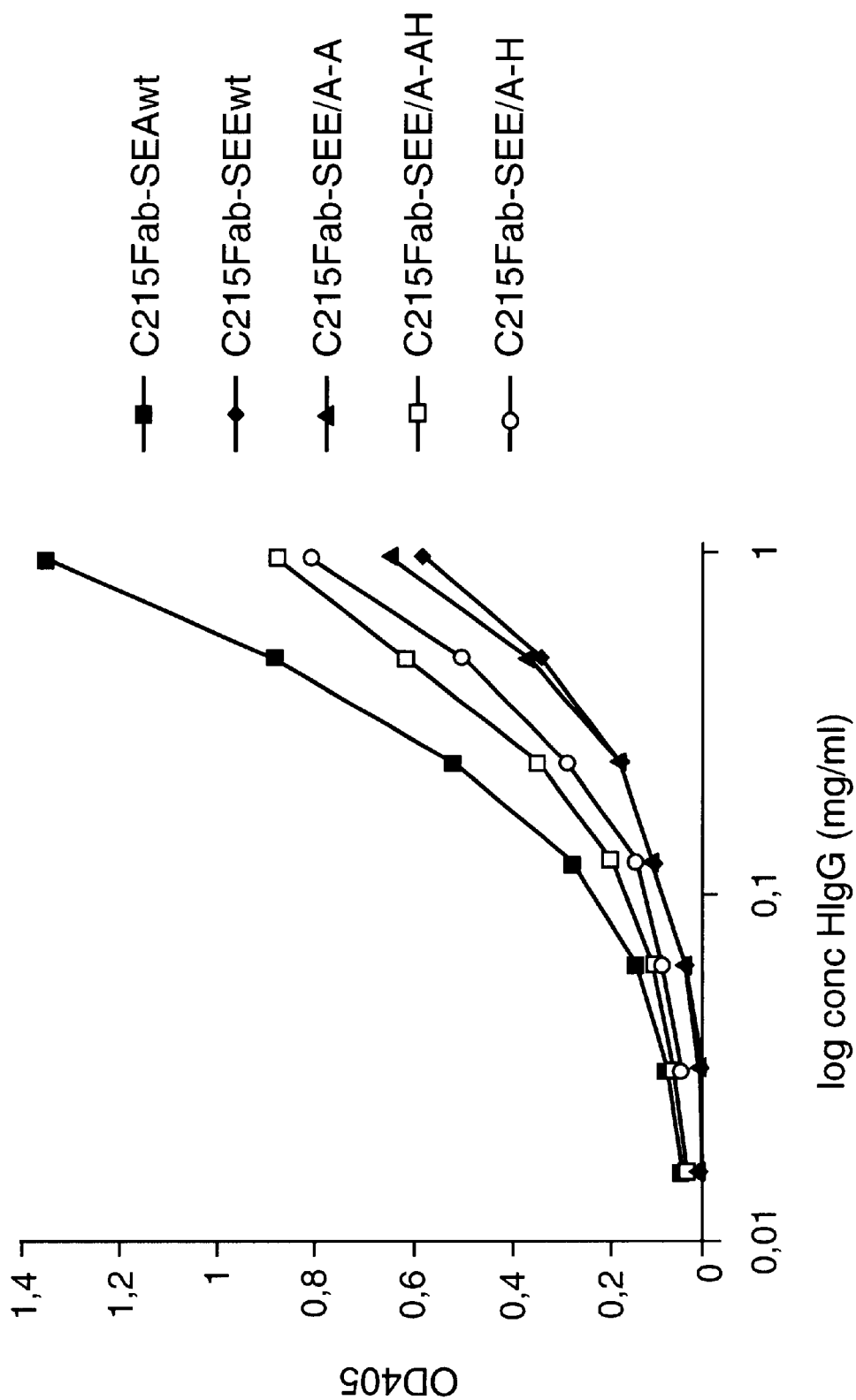

FIG. 7. Seroreactivity in a human Ig pool (Pool of >5000 sera from healthy donors in Southern Europe against C215Fab-SE fusion proteins. Serially diluted human Ig was allowed to interact for 1 h at room temperature with C215Fab-SEAwt, C215Fab-SEEwt, C215Fab-SEE/A-A, C215Fab-SEE/A-H and FabSEE/A-AH. Immobilized to the micro titer plates at a concentration of 1 ng/well. Correction for C215Fab binding to serum proteins was made by subtracting the OD-value for C215Fab at each point. Each point represents the mean of duplicate samples. For further details see Materials and Methods.

THE INVENTION

The first aspect of the invention is a method for the treatment of a disease in a mammal by activation of its immune system through administration of a therapeutically effective (immune activating) amount of a modified, preferably chimeric, superantigen. The mammal is preferably a human. The diseases in question are mostly associated with cells expressing on their surface a target structure binding to the superantigen. The target structure is in most cases different from the TCR epitope normally binding to superantigens. Binding to the target structure permits also binding to TCR and T cell activation. Illustrative examples are MHC class II antigens and other cell surface structures that may be expressed on cells associated with the courses of diseases. Illustrative diseases are cancers (such as carcinoma, sarcoma, and melanoma), viral infections, parasitic infestations and autoimmune diseases. The cells expressing the target structure may also be cells that in some way control the development of the disease to be treated.

The characteristic feature of the method is that one employs a modified superantigen in which one or more amino acid residues in a region (region I) providing for binding to a subset of T cells via a polymorphic TCR chain, in particular TCRVβ, in a wild-type superantigen (SA I) has been replaced with a respective amino acid residue retaining superantigen activity to the so modified superantigen. The presently preferred embodiments refer to a chimeric superantigen in which one or more amino acid residues in a region (region I) of a first wild-type superantigen (SA I) have been replaced with the corresponding one or more amino acid residues in a corresponding region (region II) of a second wild-type type superantigen (SA II). The regions I and II differ with respect to amino acid sequences. The superantigens I and II have been selected so that the regions I and II can replace each other without killing the superantigen function. In this context one has to account for the fact that a certain region I alone may not be interchangeable with the corresponding region of another wild-type superantigen although when interchanged together with other regions determining TCR binding and T cell activation, the result becomes a functional active superantigen. The regions concerned normally comprise less than 20 residues, in particular for superantigens analogous to SEA. The replacing amino acid residue thus is different from the replaced residue, and conceivably includes also conserved substitutions and other amino acid substitutions leading to funtionally active modified superantigens allowing binding to TCRVβ and activation of a subset of T cells. This means that the inventively modified superantigens in its broadest sense encompass any modified superantigen in which one or more amino acids in the aforementioned regions have been functionally replaced.

The term "conserved substitution" refers to replacement of an amino acid residue by a chemically similar residue, e.g. a hydrophobic residue for a separate hydrophobic residue, a charged residue for a separate charged residue etc.

As superantigens I, II etc, the staphylococcal enterotoxins, in particular those that coordinate zinc, were at the priority date preferred, i.e. SEA, SEE, SED and possibly also SEH.

The regions involved may have either of the above-mentioned functions (see the heading "The Discovery that has resulted in the Invention" and the Experimental Part):

1. A great impact on the superantigen activity as such and a limited effect on the TCR specificity, in particular on Vβ specificity. For SEA-type superantigens this means region A (SEQ ID NO. 9) (amino acid positions 20–27).
2. A profound effect on the specificity with respect to binding to polymorphic TCR chains, such as the Vβ chain. For SEA-type of superantigens this means regions C (SEQ ID No. 13) (amino acid positions 60–62), F (SEQ ID No. 19) (amino acid positions 110–126) and H (SEQ ID No. 23) (amino acid positions 200–207).

For SEA-like superantigens this means one or more of the substitutions (applied to grafting from SEA to SEE; SEE/A chimeras):

Region A: R20G, N21T, S24G, R27K

Region C: G60D, P62S

Region F: H111R, H114Q, G115Y, F117Y, G118N, S124V, G126D

Region H: D220G, P206S, D207N

At the priority date it was preferred to carry out all substitutions for each region. For other superantigens, analogous substitutions between corresponding positions/regions could conceivably also be carried out.

Typically one could start from one first superantigen, like SEE and SED, and then replace one or more of its unique Vβ binding regions with the corresponding region(s) of a second superantigen (e.g. SEA), the first and second superantigens preferably being selected so that the antibody titer in normal human sera for the first superantigen is lower than for the second superantigen. For SEA and SEE chimeras, the best modes correspond to the chimeras SEE/A-A, SEE/A-AH, and SEA/E-BDEG, with absolute preference for SEE/A-A. See the experimental part and the figures.

Together with the regions A, C, F and H also amino acid residues at other parts can be exchanged. One type of exchange is to reduce the class II binding ability, because this property is associated with common side effects encountered in superantigen therapy (general immune activation with concomitant systemic release of tumor necrosis factor (TNF) and interferon-γ). For superantigens such as SEA, SED and SEE, positions that are important for the ability to coordinate zinc ions may preferably be changed, i.e. positions 225 and 227, for instance in SEA mutation H225A and in particular D227A will have a positive impact on reducing toxic side effects. (see Abrahmsén et al WO9601650 and Fraser et al 1993).

Other substitution may be performed althroughout the molecule as long as they do not destroy the superantigen function, for instance conserved substitutions, in particular outside regions involved in the binding to class II and TCR. A change in the DNA sequence for altering the MHC class II binding or any other change on the DNA level may be carried out either before or after the change in regions providing for binding to TCR. These other types of modifications can equally well have been introduced prior to the amino acid replacement in Region I. In the context of the present invention, the concept of using a "wild-type superantigen" at the start of the modification according to the claims thus primarily refers to the wild-type amino acid sequence in region I outside of which prior modifications may have taken place.

Construction of chimeric and mutated superantigens can be carried out according to techniques well-known in the art.

The switch from a region specific for one superantigen to the corresponding region in another superantigen is done on the genomic level and may be accomplished by replacing a complete sequence or by point mutations of those specific bases that are required to end up in the desired amino acid sequence. See for instance the experimental part and also the prior art references cited above. The term "mutation" comprises replacing, inserting or removing one or more amino acid residues by modifying the DNA sequence coding for the protein to be mutated.

The superantigen to be used in the inventive method can be a non-conjugated superantigen modified as described above, i.e. a modified superantigen lacking a specifically attached target-seeking moiety but with a pronounced ability to bind to both MHC class II antigens and a subset of T cells via TCR. More preferably the modified superantigen, preferably a chimeric superantigen, is conjugated to a target-seeking moiety. In the latter case the preferred variants are fusions between the target-seeking moiety and the modified superantigen. The conjugates as such are novel and are a separate aspect of the invention.

The structures of the inventive conjugates are analogous to earlier known antibody-superantigen conjugates (Dohlsten et al WO9201470; Abrahmsén et al WO9601650, both publications hereby being incorporated by reference), i.e. the conjugates often comply with the formula:

T-B-SA(m)

where T represents the target-seeking moiety, SA(m) the modified, preferably chimeric, superantigen as defined above, and B is a covalent bridge linking T and SA(m) together. T may in principle contain further superantigen moieties (SA(m)), and SA(m) further target-seeking moieties, although in the preferred conjugates there is only one target-seeking moiety and one modified superantigen moiety as defined above.

T can in principle be any structure that is able to bind to a cell surface structure, preferably a disease specific structure. The structure against which T is directed is usually different from (a) the Vβ chain epitope to which SA(m) binds, and (b) the MHC class II epitopes to which superantigens bind. The target-seeking moiety is primarily selected among interleukins (e.g. interleukin-2), hormones, antibodies including antigen binding fragments of antibodies, growth factors etc. See for instance Woodworth, Preclinical and Clinical development of Cytokine toxins presented at the conference "Molecular approaches to cancer Immunotherapy", Ashville, N.C., Nov. 7–11, 1993.

At the priority date, it was preferred that T was an antibody (Fab, F(ab)$_2$, Fv, single chain antibody etc), with particular emphasis for antibody active fragments (such as Fab), directed towards the so called C242 epitope (Lindholm et al., WO9301303) or more preferably towards the binding epitope for the lung cancer specific 5T4 antibody (Stern et al., WO8907947). This, however, does not exclude that other cancer specific antibodies may function equally well or even better. The term "antibody" comprises monoclonal as well as polyclonal variants, with preference for monoclonal preparations.

T may also be directed towards unique structures on more or less healthy cells that regulate or control the development of a disease.

The bridge B may be selected as previously described (Dohlsten et al WO9201470; and Abrahmsén et al WO9601650), i.e. B shall preferably be hydrophilic and exhibit one or more structure(s) selected among amide, thioether, disulphide etc. The most prominent bridges are those obtained by recombinant techniques, i.e. the conjugation takes place at the genomic level. In such cases oligopeptide bridges containing hydrophilic amino acid residues, such as Gln, Ser, Gly, Glu, Pro, His and Arg are preferred. Particularly preferred Bs are peptide bridges consisting of 1–10 amino acid residues, with absolute preferences for 3–7 amino acid residues. A typical bridge is the tripeptide GlyGlyPro, SEQ ID NO 1.

The manufacture of the novel inventive conjugates may be carried out in principle according to two main routes: 1. Recombinant techniques and 2. Chemical linking of a target-seeking moiety T to a modified, preferably chimeric, superantigen (SA(m)) as defined above. These methods are well recognized for the ordinary skilled worker and comprise a large number of variants.

Chemical linking of a modified non-conjugated superantigen to a target-seeking moiety T often utilizes functional groups (e.g. primary amino groups or carboxy groups) that are present in many positions in the compounds. It follows that the final product will contain a mixture of conjugate molecules differing in linking positions, as well as hetero- and homo-conjugates.

For recombinant conjugates (fusion proteins) the obtained conjugate substance will be uniform with respect to the linking position. Either the amino terminal of the chimeric superantigen is linked to the carboxy terminal of the target-seeking moiety or vice versa. For antibodies, such as intact antibodies and antigen-binding fragments (Fab, Fv, single chain antibodies etc), either the light or the heavy chain may be utilized for fusion. At present time recombinant conjugates are preferred, with utmost preference for Fab fragments and linking of the amino terminal of the chimeric superantigen to the first constant domain of the heavy antibody chain (CH1), without exclusion of the analogous linking to the light chain or to the VH land VL domain that also may give quite good results.

The main host cell for large scale recombinant production of the inventive modified superantigens (fused forms as well as non-conjugated forms) is E. coli. This host provides for in principle two routes: intracellular production and secretion. The latter variant is preferred because it offers purification of correctly folded proteins from the periplasma and from the culture medium. The above does not exclude that it is possible to produce active conjugates also in other host cells, e.g. eukaryotic cells, such as yeast or mammalian cells.

Pharmaceutical Compositions, Dosage and Routes of Administration

A third aspect of the instant invention is pharmaceutical compositions containing the inventive modified, preferably chimeric, superantigens as defined above (both conjugated and non-conjugated forms). The compositions contemplated are known in the field, except that now they contain the instant inventive superantigen. Thus, the compositions may be in the form of a lyophilized particulate material, a sterile or aseptically produced solution, a tablet, an ampoule etc. Vehicles such as water (preferably buffered to a physiologically acceptable pH value by for instance PBS) or other inert solid or liquid material may be present. In general terms the compositions are prepared by the conjugate being mixed with, dissolved in, bound to, or otherwise combined with one or more water-soluble or water-insoluble aqueous or non-aqueous vehicles, if necessary together with suitable additives and adjuvants. It is imperative that the vehicles and conditions must not adversely affect the activity of the modified superantigen.

Normally the inventive superantigen will be sold and administered in predispensed dosages, each one containing an effective amount of the conjugate that, based on the result now presented, is believed to be within the range of 10 ng–50 mg, such as within 10 ng–1 mg or within 10 μg–50 mg. The exact dosage will vary from case to case depending on the patient's weight and age, route of administration, type of disease, target-seeking moiety, superantigen, linkage (-B-) etc.

The administration routes will be those commonly contemplated within the field, i.e. a target cell killing effective amount or therapeutically active amount of a superantigen modified according to the invention is brought into contact with the target cells. For the indications specified above this mostly means parenteral administration, such as injection or infusion (subcutaneously, intravenously, intraarterial, intramuscularly, intraperitoneal) to a mammal, such as a human being. The modified, preferably chimeric, superantigens contemplated may be administered locally or systemically.

By the term "target killing effective amount" is contemplated that the amount is effective in activating and directing T cells to destroy target cells.

The preferred administration route at the priority date is the same as contemplated for the superantigen conjugates according to Dohlsten et al WO9201470 and Abrahmsén et al WO9601650. This means 1–5 hours' intravenous infusion (preferably 4 hours) per day combined with a fever-reducing agent (paracetamol). The administration is to be repeated during some days, for instance 4 days, with care consideration taken for the risk of boostering antibodies directed towards the conjugate.

The inventive superantigens may be administered either as the main therapy or in preferred modes as adjuvant therapy in connection with surgery or other drugs.

In the context of therapy we have found that antibody preparations that are pure with respect to non-covalently associated heavy and light antibody chains provide advantages over preparations that contains antibodies in which the chains are linked together via cystine linkages. Accordingly a fourth aspect of the invention is the therapeutic use of an antibody preparation, in particular an Fab preparation, in which the cysteine residues linking the chains together have been replaced by an amino acid not permitting disulfide formation, for instance serine. The most preferred antibody specificities for this aspect of the invention were at the priority date the C242 mab (Lindholm et al., WO9301302) and the 5T4 mab as defined in the references cited above. In the preferred variants one of the antibody chains is fused to a superantigen that is capable of activating a subset of T cells in a Vβ specific manner as described above. The superantigen may be a wild-type, a chimer, or a point-mutated version (and combination thereof) as described above or by Dohlsten et al WO9201470 or by Abrahmsén et al WO9601650. This aspect of the invention also comprises pharmaceutical compositions as described above, but containing an antibody preparation as defined for this aspect of the invention instead of a chimeric superantigen.

At the priority date it was preferred to use the Fab fragment 5T4 antibody (Stern et al, WO8907947) in combination with the SEE/A-A chimera with the mutation D227A. The preferred Fab fragment was mutated in both chains in the position providing interchain disulfide linkage (cys to ser). In order to increase the yield of the antibody/fusion protein when produced in *E coli,* mutations were also carried out in the Vkappa chain at certain positions. See the experimental part.

Materials and Methods
Construction of SEA/SEE Chimeric Genes

Construction of SEA/SEE chimeras were made using the polymerase chain reaction (PCR) based method, sequence overlap extension (Horton et al). PCR reactions were performed with UITma (Perkin-Elmer) according to manufactures recommendations. PCR produced fragments were cloned in PCR-script (Stratagene, USA) and sequenced to verify the correct sequence. The chimeric superantigen genes were then subcloned in the expression vector pKP889 (Abrahmsén et al 1995), fusing the SE constructs to the heavy chain portion to the Fab fragment of the murine monoclonal antibody C215. The SEA and SEE recombinant fusion proteins were produced as full length polypeptides in accordance with the consensus sequence for signal peptide cleavage (von Heijne 1986).

Protein Expression and Purification

The *Escherichia coli* K12 strain UL635 was used for expression of the Fab-SE fusion proteins and the SEA mutants as described earlier (Abrahmsén et al 1995). Fab-SE fusion protein was harvested by centrifugation at 5000 g and the supernatant fraction was subjected to purification on protein G Sepharose (Pharmacia Biotech AB, Uppsala, Sweden) as earlier described (Abrahmsén et al 1995). The purity of the affinity purified Fab-SE variants were >90% pure when analyzed by SDS-PAGE.

Cells

The human B-cell lymphoma cell line Raji and human colon carcinoma Colo 205 were cultured in complete R-medium (RPMI-1640 supplemented with 10% fetal calf serum (Gibco BRL, Life Technologies, Ltd. Paisley Scotland) 1 mM glutamine; HyClone Europe, Ltd. Cramlington, $5\times10^{-5}$ M β-mercaptoethanol; ICN Biomedicals INC. Costa Mesa Calif., 0.1 M $NaHCO_3$; Seromed Biochrome, $1\times10^{-2}$ M Hepes buffer; HyClone Europe, Ltd. Cramlington., 0.1 mg/ml gentamycine; Biological Industries Kibbutz Beit Haemek Israel, $1\times10^{-3}$ M sodium pyruvate; HyClone Europe, Ltd. Cramlington). CHO cells transfected with human C215 and CD80 molecules were cultivated in complete R-medium supplemented with 0.5 mg/ml Geniticin (G418) Gibco BRL, Life Technologies, Ltd. Paisly Scotland). Peripheral blood mononuclear cells (PBM) were prepared from heparinized blood from normal donors. The cells were isolated by density centrifugation over Ficoll-Paque as previously described (Dohlsten et al 1991). Human T lymphocytes were purified to homogeneity by positive selection using MiniMACS columns in conjunction with magnetic beads coated with monoclonal antibodies specific for human CD4 and CD8 (Miltenyi Biotec GmbH, Germany) according to the manufacturers specifications. Human SEA and SEE reactive cell lines were generated as previously described (Dohlsten et al 1994). Human TCR Vβ22 expressing cell line was generated from a primary stimulated SEA reactive cell line using positive selection with magnetic Dynabeads (Dynal A.S., Norway) coated with TCR Vβ22 specific monoclonal antibody (Immunotech, France). Enriched cells contained >95% TCR Vβ22$^+$ T cells as determined by flow cytometry (data not shown). Murine T-cell hybridomas (I1B3, 2B4 and 11.40) were generated as described (Fleury et al 1991).

Cytotoxicity Assay

Cytotoxicity was measured in a standard $^{51}Cr$ release assay after 4 or 6 hours as previously described (Dohlsten et al 1991). Human Colo205 or Raji cells were used as target cells. The effector cells, either SEA or SEE reactive human T cell lines or TCR Vβ22 cell lines, were added at an effector to target ratio of 30:1. $^{51}Cr$-labeled target cells were used in the cytotoxicity assays at 2500 cells/200 ml complete medium in V-bottomed microtiter wells. C215Fab-SEA/E hybrids were added at various concentrations as indicated and $^{51}$Cr release was measured in a g-counter. The percentage specific cytotoxicity was calculated as 100×[(c.p.m. experimental release–c.p.m. background release)/(c.p.m. total release–c.p.m. background release)].

Lymphocyte Proliferation Assays

To measure proliferation $10^5$ human T cell responders were incubated at 37° C. with $10^4$ irradiated (20.000 Rad) stimulator cells in 200 ml complete medium in U-shaped 96-well microtitre plates with varying amounts of C215Fab-SEA/E hybrids for 72 hours. Proliferation was estimated by incorporation of [$^3$H]-thymidine as described (Dohlsten et al 1988).

Analysis of Fab-SAg Induced IL-2 Production

Murine T-T hybridoma cells ($10^5$) were incubated in 200 ml complete R-medium with C215Fab-SEA/E chimeric proteins in the presence of 2×$10^4$ Raji stimulator cells. After 48 hours, supernatants were harvested and analyzed for presence of murine IL-2. Briefly, cytokine content was analyzed using rat anti-mouse cytokine mAb as catcher antibodies. Purified rat anti-mouse IL-2, biotin-labeled rat anti-mouse IL-2, rIL-2 was purchased from PharMingen (San Diego, Calif.). Biotin-labeled anti-cytokine mAb, Vectastain ABC kit (Vector Laboratories, CA) and peroxidase substate kit (Bio-Rad Laboratories, CA) were used for detection of cytokines. The absorbance was determined in a ImmunoReader NJ2000 (InterMed Roskilde, Denmark) at 405 or 450 nm.

Mutation of 5T4 Fab

Construction of a Vector for Expression of 5T4Fab-SEA in *E. coli*

The Fv-encoding portions of 5T4 were cloned from the 5T4 hybridoma, obtained from Dr Peter Stern (Stern et al., WO8907947). In more detail: cDNA was made from the mRNA, regions of the entire variable domains and parts of the signal sequences as well as the first constant domain of the heavy chain and the constant domain of the light chain were amplified by PCR. The oligonucleotides 5'-CAATTTTCTTGTCCACCTTGGTGC-3' (SEQ ID NO: 2) and 5'-ACTAGTCGACATGGATGGAGCTTTATCATIyT CTT-3' (SEQ ID NO 3)

were used for the heavy chain, resulting in a 553 bp fragment, while the oligonucleotides 5'-ACTAGTCGACATGGGCITCAAGATGGAGTCA CAkwyyCwGG-3' (SEQ ID NO: 4) and

5'-GCGCCGTCTAGAATTAACACTCATTCCTGTTGAA-3' (SEQ ID NO: 5)

were used for the light chain, yielding a 724 bp fragment. For each chain three separate clones were sequenced and found to be identical. DNA fragments suitable for insertion into the expression vector were obtained in a second PCR step. In order to assemble a Fab-expression plasmid, the variable regions of 5T4 were fused to sequences coding for constant regions from the murine IgG1/k antibody C242 mab (Lindholm et al, WO9301302). A region coding for a superantigen derived from staphylococcal enterotoxin A (SEA) was fused after the heavy chain. The verified sequence for the Vkappa chain antibody framework for the 5T4 antibody is given in the results.

Mutagenesis of 5T4

Seven amino acid replacements were introduced in the regions coding for the antibody framework. These were Phe10Ser, Thr45Lys, Ile63Ser, Tyr67Ser, Phe73Leu, Thr77Ser and Leu78Val. Similarly, the Cys residues in either chain involved in the interdomain disulfide bond were replaced by serine residues resulting in the mutations Cys458Ser in the heavy chain and Cys214Ser in the light chain. The mutations were introduced using PCR-based mutagenesis and the DNA sequence obtained was confirmed using sequencing.

Fermentor Expression and Purification of 5T4Fab-SEA

The expression plasmid contains the kanamycin resistance gene and a lacUV5-promoter that may be induced with IPTG. The fusion proteins were purified from the clarified culture medium using protein G Sepharose and SP-Sepharose (Pharmacia Biotec, Uppsala, Sweden) and formulated in citrate buffer using Sephadex G-25, essentially as described. Characterization using SDS-PAGE, reverse phase HPLC and mass spectrometry showed that the purified fusion protein was more than 95% pure and had the correct molecular mass.

Results: Superantigen Modifications

Figure 1:
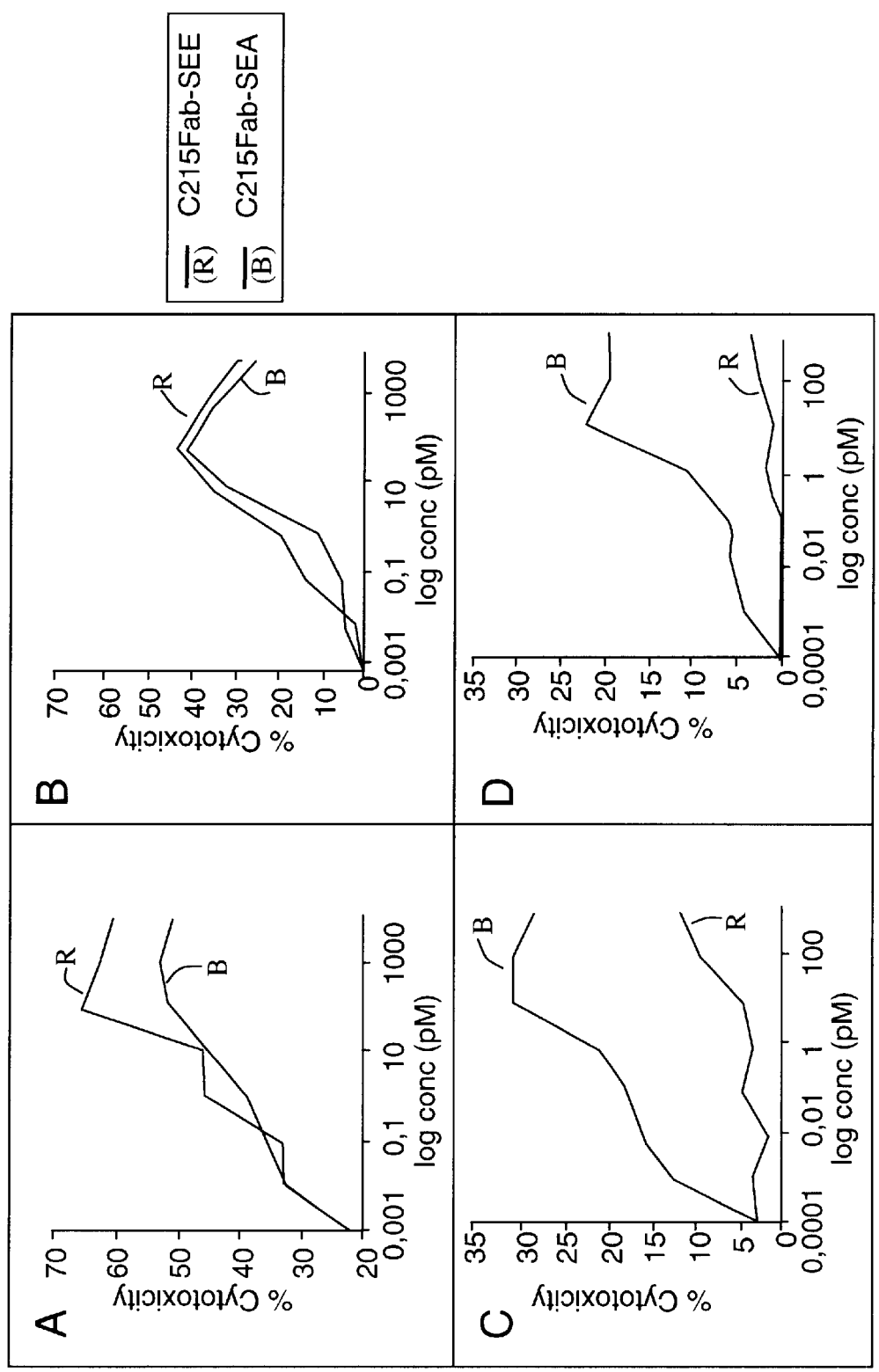
FIG. 1.

The superantigen dependent cellular cytotoxicity (SDCC) of C215Fab-SEA and of C215Fab-SEE against MHC class II$^+$ Raji cells, was analyzed using SEA- and SEE-reactive human T cells as effector cell lines. Despite the difference in Vβ specificity between SEA and SEE both superantigens exhibited induction of comparable degree of cytotoxicity with both effector cell lines (FIG. 1). To discriminate between effects of MHC class II presentation and direct effects of SEA and SEE in TCR recognition, they were examined in superantigen-antibody dependent cellular cytotoxicity (SADCC) against C215 expressing Colo205 cells. In this assay the Fab moiety directs the fusion protein to C215-expressing target cells and results in the presentation of fused SE molecules to cytotoxic T-cells (CTL) independent of MHC class II molecules (Dohlsten et al 1994). Despite >80% amino acid sequence identity between SEA and SEE the TCR interaction of SEA and SEE displays qualitative differences in this type of assay. The C215Fab-SEA fusion protein retains its ability to direct SEA and SEE reactive CTL against the MHC class II$^-$ target cells (FIG. 1) while C215Fab-SEE fails to induce cytotoxicity of the, MHC class II$^-$ target cells, neither with SEA nor with SEE reactive CTL (FIG. 1).

It has previously been reported by other investigators that the differences in Vβ specificity between SEA and SEE primarily relates to a three amino acid difference in the loop preceding and in the irregular a5 helix (Irwin et al 1992, Hudson et al 1993, Fraser et al 1993, and Mollick et al 1993). The difference in respect to TCR interaction reported in this investigation is not related to altered TCR Vβ specificity since the ability of C215Fab-SEA to induce MHC class II independent cytotoxicity is not restricted to SEA reactive CTL but is also seen with SEE reactive CTL.

Figure 2:
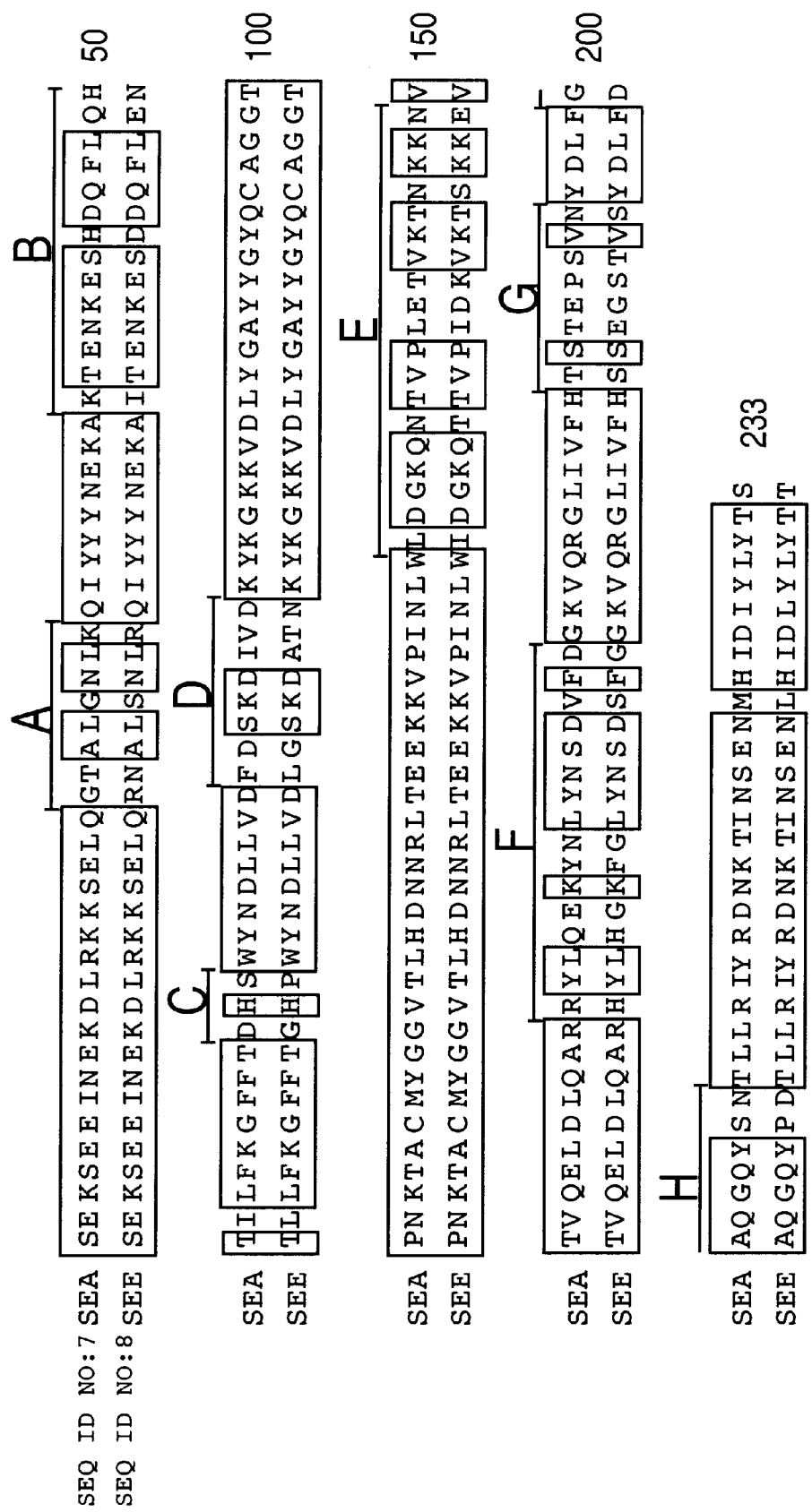
FIG. 2. Homology alignment of SEA and SEE. SEA/SEE variable regions close to the TCR binding site (A, C, F and H) and variable regions close to the two MHC class II binding sites.
Figure 3:
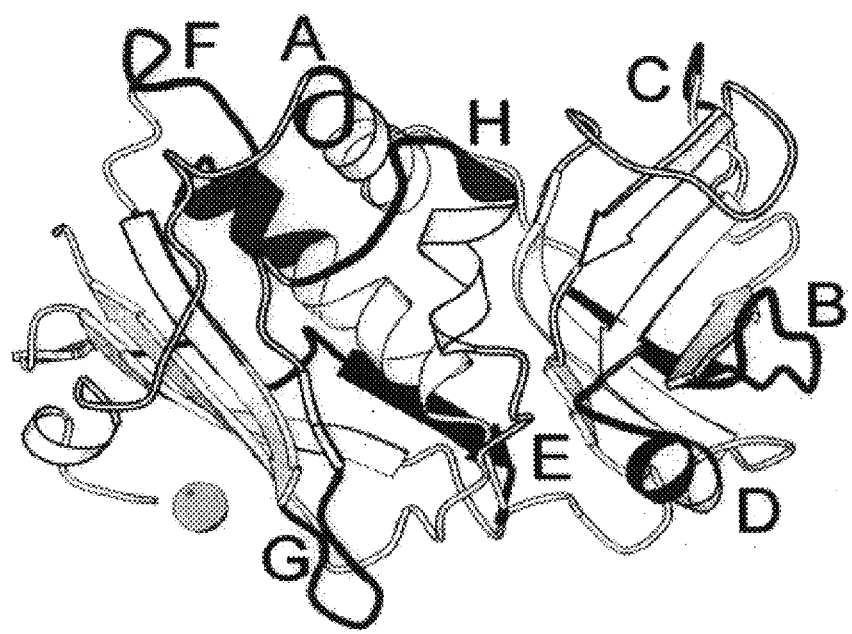
FIG. 3. Molscript model (Kraulis, 1991) of the SEA crystal (Schad et al. 1995). SEA/SEE variable regions close to the TCR binding site (A, C, F and H) and variable regions close to the two MHC class II binding sites. The zinc ion is a round ball.
Figure 4:
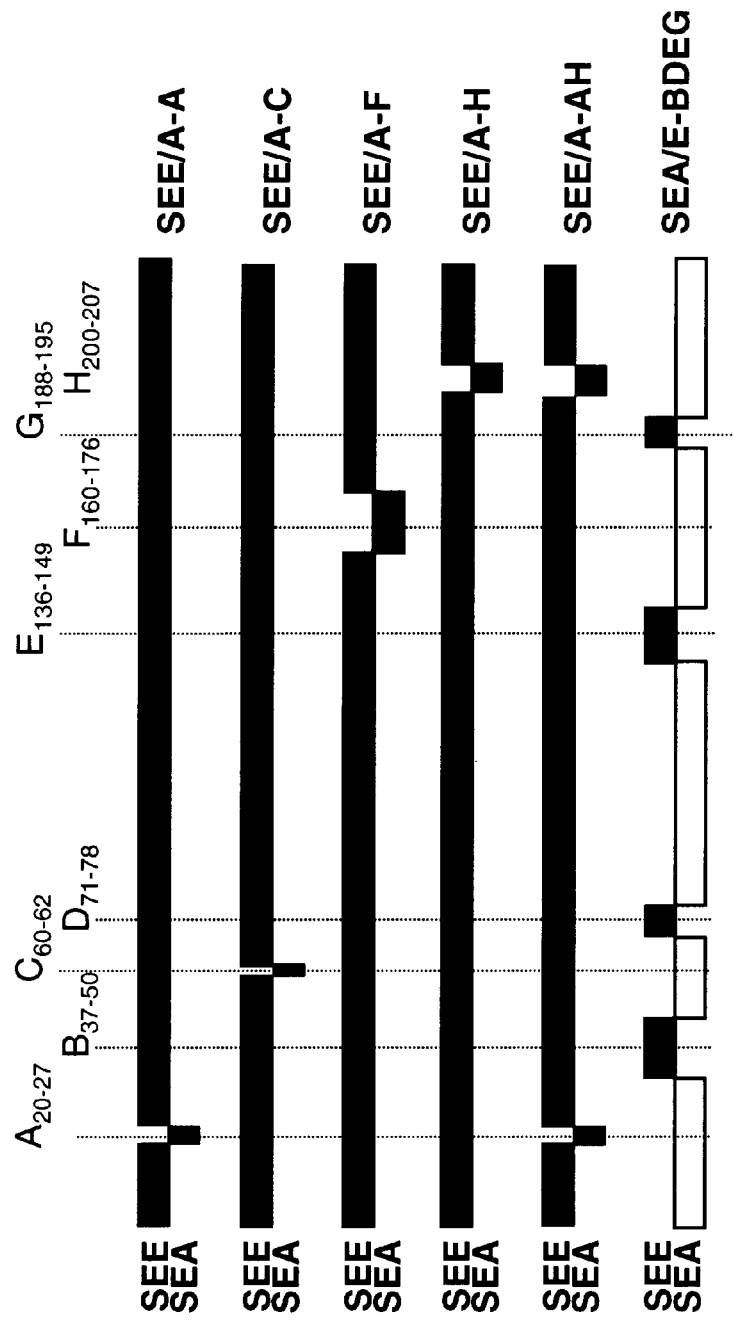
FIG. 4. Schematic representation of chimeric SE molecules. Stretches of SEA sequence are depressed. SEA/SEE variable regions are represented by A, B, C, D, E, F, G and H.

Sequence homology analysis of SEA and SEE (FIG. 2) reveals that the non-identical amino acid residues are concentrated to eight distinct regions. Outside these eight regions, making up to 34% of the sequence, the identity of the two SE's is 97%, with conserved amino acid substitutions accounting for the remaining differences. Four of the non-homologous regions are structurally close to the two MHC class II binding sites (B (Sequence ID Nos. 11 and 12), D (Sequence ID Nos. 15 and 16), E (Sequence ID Nos. 17 and 18) and G (Sequence ID Nos. 21 and 22)), and are not likely to interact with the TCR (FIG. 3). The additional four regions (A: AA 20–27 (Sequence ID Nos. 9 and 10), C: 60–62 (Sequence ID Nos. 13 and 14), F: 161–17 6 (Sequence ID Nos. 19 and 20), and H: 200–207 (Sequence ID Nos. 23 and 24)) are located on the edge of the molecule (FIG. 3), in the vicinity of the TCR binding site, located in the groove between the two subdomains (Kappler et al 1992). To investigate the qualitative difference in TCR recognition between SEA and SEE we made hybrid proteins by grafting the regions from SEA to SEE as single region chimeras (SEE/A-A, -C, -F, H) as double region hybrids (SEE/A-AH) and by grafting the regions located in the vicinity of the MHC class II binding sites on SEE to SEA (SEA/E-BDEG) (FIG. 4). All of the chimeric SEs were expressed as C215Fab fusion proteins to be able to detect differences with respect to their activity in the absence of MHC class II.

The SEA/E Hybrid Proteins in Fusion with the C215Fab Moiety Displays Difference in Fab Targeted Cytotoxic Assays The SDCC activity of C215Fab-SEE/A hybrid proteins against MHC class II$^+$ Raji cells were analyzed using SEA-reactive human T cells as effectors. The $EC_{50}$ values of all C215Fab-SE hybrids as well as the C215Fab-SEAwt and -SEEwt falls in the margin of errors (e.g. $10^{-12}$–$10^{-11}$ M, FIG. 5). The only detectable difference is slightly reduced plateau of the C215Fab-SEE/A-AH hybrid, indicating a loss of responding T cells. On the other hand in SADCC experiments where the cytotoxicity is directed towards MHC class II$^-$/C215$^+$ Colo 205 cell line, only C215Fab-SEE/A-A, C215Fab-SEE/A-AH and C215Fab-SEA/E-BDEG induced comparable cytotoxicity as the C215Fab-SEAwt (FIG. 5). The C215Fab-SEE/A-F hybrid is able to induce C215 targeted cytotoxicity at higher concentrations ($EC_{50}$>$10^{-10}$ M). Although the C215Fab-SEE/A-H hybrid is able to induce C215 targeted cytotoxicity with similar half maximal concentration as C215Fab-SEAwt (e.g. $EC_{50}$ $10^{-13}$M), the absolute level of cytotoxicity is strongly reduced (FIG. 5). This difference could be a consequence of a restricted Vβ specificity of the C215Fab-SEE/A-H while the ability of inducing C215 targeted cytotoxicity prevails in the responding T cell sub-population. To further investigate this notion we prepared human Vβ22 oligoclonal CTL line. Human Vβ22 are analogous to murine Vβ3 in the respect that it is a SEA non SEE specific Vβ family. It has previously been shown (Mollick et al 1993) that the major contribution of SEA and SEE Vβ is primarily resides in the three amino acid difference between SEA and SEE in region H (AA 200–207). In SDCC assays against MHC class II$^+$ Raji targets, using the Vβ22 oligoclonal CTL line as effectors, only hybrids containing the SEA-H region are able to give C215Fab-SEAwt-like response (e.g. C215Fab-SEE/A-H, C215Fab-SEE/-AH and C215Fab-SEA/E-BDEG, FIG. 6). The C215Fab-SEE/A-A hybrid, that was able to induce a full SDCC response with whole CTL populations as effectors is in this assay strongly reduced both in half maximal concentration and in the plateau (FIG. 6). When the cytotoxicity of the Vβ22 CTL is directed towards the MHC class II$^-$/C215$^+$ Colo 205 cell line only hybrids containing both SEA-A and SEA-H (e.g. C215Fab-SEE/A-AH and C215Fab-SEA/E-BDEG) regions are able to induce a cytotoxic response, comparable to a C215Fab-SEAwt (FIG. 6). The hybrid containing only the SEA region A (C215Fab-SEE/A-A) induces a lower level of cytotoxicity with a comparable EC50 value. This indicates that the remaining activity seen with the C215Fab-SEE/A-H hybrid in SADCC with the whole T cell population as effectors is not a consequence of the hybrid induced response in restricted population of T cells. A more likely explanation for the observation is that the ability to induce a SADCC response of the C215Fab SE hybrid proteins is primarily residing in the SEA-A region with a minor contribution from the SEA-H and -F regions. There is no evidence that this quality is restricted to any subset of T cells in the combined SEA-SEE responding T cell population, since C215Fab SEA is able to induce the same response with as well with SEE reactive CTLs and C215Fab-SEE/A-A is able to fully to reconstitute the response seen with C215Fab-SEA.

The SEA/E Hybrid Proteins in Fusion with the C215Fab Moiety Displays Difference in Fab Targeted Proliferation Assays It has been previously shown that purified resting human T cells are induced to proliferate by presentation of C215Fab-SEA on a MHC class II$^-$/C215$^+$/CD80$^+$ cell line (Lando et al 1993). The ability of C215Fab-SEA to induce MHC II independent proliferation is however markedly reduced with C215Fab-SEE (Tab. 1). To investigate if this difference in quality shows the same confinement to SEA region A, as was seen with SADCC, we investigated the proliferative capacity of C215Fab-SE hybrids, presented by either CHO-DR1$^+$/CD80$^+$ or CHO-C215$^+$/CD80$^+$ transfected cell lines, on purified resting human T cells. When presenting the Fab-SE conjugates on CHO-DR1$^+$/CD80$^+$ no differences between the different SE proteins were noted (data not shown). However grafts of SEA region A, C and H in SEE potentates the proliferative activity compared to C215Fab-SEE. The best results were obtained by grafting SEA regions A and H, indicating a important role for region A as was seen for the MHC class II independent cytotoxicity. By using a negative selection it is possible that the differences between Fab-SEA and -SEE would be more prominent.

Vβ Specificity of SE-hybrids

To further investigate if the C215Fab-SEA/SEE hybrid-fusion proteins were associated with a certain Vβ specificity we used SEA reactive murine T cell hybridomas expressing Vβ1, Vβ3 and Vβ11. It is obvious from the data obtained that all of the regions investigated, directly or indirectly, affects the interaction with the TCR. By grafting SEA regions C and F in C215Fab-SEE the activity towards the SEA and SEE cross reactive Vβ1 hybridoma I1B3 is destroyed. The same chimeras seems to have no or minor effects on the activity of Vβ3 and Vβ11 hybridomas (2.B4 and 11.40) in comparison with C215Fab-SEE. By grafting SEA region A in C215Fab-SEE the activity towards Vβ3 (2.B4) is enhanced by at least a factor 100, in comparison to C215Fab-SEE. More pronounced effects are seen with the same cell line by grafting SEA region H in C215Fab-SEE. This pronounced effect on the influence of Vβ3 specificity by SEA region H has also been noted by earlier investigations (Mollick et al 1993). The same chimera however (C215Fab-SEE/A-H), seems to reduce the activity towards the SEA/SEE cross reactive Vβ1 and Vβ11 hybridomas (I1B3 and 11.40) by a factor 10. In conclusion, the TCR interaction of SEA seems to involve all of the SEA-SEE, variable regions A, C, F and H.

Seroreactivity

The seroreactivity in human serum samples towards the chimeric SEs was investigated both in pooled samples from different parts of the world as well as in individual serum samples. By grafting both SEA regions A and H in SEE we obtained an intermediate seroreactivity (FIG. 7). A similar seroreactivity was also seen against the chimera C215Fab-SEE/A. However, single grafts of SEA region A in SEE (C215Fab-SEE/A-A) gave a C215Fab-SEE like seroreactivity, indicating that SEA region H is responsible for the remaining seroreactivity against C215Fab-SEE/A-AH. This indicates that the SEA region H is part of dominating antigenic epitope in SEA. The seroreactivity from pooled serum samples from other parts of the world (Japan and USA) as well as 14 individual samples from Sweden all confirms the same general pattern (data not shown).

Results: Mutations of the Fab Part of the Fusion Proteins Expression of 5T4FabSEA-constructs The production level in *E.coli* of 5T4Fab-SEA in the fermenter was found to be significantly lower than other Fab-superantigen constructs previously studied in our lab. Two types of modifications were therefore introduced to increase the production level. Firstly, seven different point mutations in the framework region of the light chain were introduced. These were Phe10Ser, Thr45Lys, Ile63Ser, Tyr67Ser, Phe73Leu, Thr77Ser and Leu78Val. Secondly, the cysteine residues making the disulfide bond connecting the heavy and the light chains were replaced by serine residues. The latter modification resulted in a three-fold increase and the 7 point mutations in an additional 12-fold increase in the production level. In addition to the significantly increased production level, removing the disulfide bond also gives a more homogenuous product since the possibility of the these reactive thiol groups to react with other thiol containing agents is excluded.

The modified 5T4 molecule was checked for affinity to its antigen as well as for biological activity in SADCC. No differences between the mutant form and the wildtype form could be detected in these assays.

The Cys/Ser mutation was also performed in the heavy and light chains of the Fab fragments of several other monoclonal antibodies. The products became homogenous and fully retained the antigen binding capability.

Sequence of region of the antibody frame work for the 5T4 Vkappa chain:

DAVMTQTPTF LLVSAGDRVT ITCKASQSVS NDVAWYQQKP GQSPTLLISY 50

TSSRYAGVPD RFIGSGYGTD FTFTISTLQA EDLAVYFCQQ DYNSPPTFGG 100 GTKLEIK (SEQ ID NO 6)

Underlined sequences are CDRs. Bold-typed positions were mutated: Phe10Ser, Thr45Lys, Ile63Ser, Ile63Thr, Tyr67Ser, Phe73Leu, Thr77Ser, Leu78Val.

| | Proliferation $EC_{50}$ (pM) |
|---|---|
| C215Fab-SEA wt | 2.2 |
| C215Fab-SEE wt | 6.9 |
| C215Fab-SEE/A–A | 0.9 |
| C215Fab-SEE/A–C | 2.8 |
| C215Fab-SEE/A–F | 5.7 |
| C215Fab-SEE/A–H | 1.0 |
| C215Fab-SEE/A–AH | 0.3 |
| C215Fab-SEA/E–BDEG | 1.6 |

| | I1B3 (MuVβ 1) $EC_{50}$ (nM) | 2.B4 (MuVβ 3) $EC_{50}$ (nM) | 11.40 (MuVβ 11) $EC_{50}$ (nM) |
|---|---|---|---|
| C215Fab-SEA | 10 | 3 | 0.05 |
| C215Fab-SEE | 10 | >1000 | 0.05 |
| C215Fab-SEE/A–A | 10 | 10 | 0.05 |
| C215Fab-SEE/A–C | >1000 | >1000 | 0.05 |
| C215Fab-SEE/A–F | >300 | >300 | 0.05 |
| C215Fab-SEE/A–H | 100 | 3 | 0.3 |
| C215Fab-SEE/A–AH | 10 | 3 | 0.3 |

Because many varying and different embodiments may be made within the scope of the inventive concept herein taught, and because modifications may be made in the embodiments herein detailed in accordance with the descriptive requirements of the law, it is to be understood that the details herein are to be interpreted as illustrative and not in a limiting sense.

REFERENCES

Abrahmsén L et al (1995) Characterization of two distinct MHC Class II binding sites in the superantigen staphylococcal enterotoxin A. EMBO J 14:2978–86.

Abrahmsén et al (1996) WO961650 (patent application).

Dohlsten et al (1988) Two subsets of human peripheral blood CD4+ T helper cells differing in the capacity to produce IL-2 and interferon-gamma can be defined by the Leu-18 and UCHL1 monoclonal antibodies. Eur J Immunol 18:1173.

Dohlsten M et al (1994) Monoclonal antibody-superantigen fusion proteins: Tumor specific agents for T cell based tumor therapy. Proc Natl Acad Sci USA 91:8945–49.

Dohlsten M et al (1991) Monoclonal antibody-targeted superantigens: A different class of anti-tumor agents. Proc Natl Acad Sci USA 88:9287–91.

Dohlsten et al (1992) WO9201470 (patent application).

Fleury S et al (1991) Mutational analysis of the interaction between CD4 and class II MHC: class II antigens. Cell 66:1037–49.

Fraser J D et al (1993) Structural model of Staphylococcal enterotoxin A interactions with MHC class II antigens. In: Huber, B T Palmer, E (eds) Current Communications in Cell and Molecular Biology 7. Cold Spring Harbour Laboratory Press, Cold Spring Harbor, N.Y.

Grossman et al (1991) Mutation of the disulfide loop in staphylococcal enterotoxin A. Consequences for T cell recognition. J Immunol 147:3274–81.

Hartwig U F et al (1993) Mutations affecting MHC class II binding of the

Horton R M et al (1990) Gene splicing by overlap extension: tailor-made genes using the polymerase chain reaction. Biotechniques 8:528–35.

Hudson et al (1993) Two adjacent residues in staphylococcal enterotoxins A and E determine T cell receptor V beta specificity. J Exp Med 177:175–84.

Hufnagle W O et al (1991) The carboxyl-terminal region of staphylococcal enterotoxin type A is required for a fully active molecule. Infect Immun 59:2126–34.

Irwin M J et al (1992) Enterotoxin residues determining T-cell receptor Vb binding specificity. Nature 359:841–3.

Kalland et al (1991) WO 9104053 (patent application).

Kappler J W et al (1992) Mutations defining functional regions of the superantigen staphylococcal enterotoxin B. J Exp Med 175:387–96.

Kappler et al (1993) WO9314634 (patent application).

Kotzin B L et al (1993) Superantigens and their potential role in human disease. Adv Immunol 54:99–166.

Kraulis P J (1991) MOLSCRIPT: A program to produce both detailed and schematic plots of protein structures. J Appl Cryst 24:946–50.

Lando P A et al (1993) Co-stimulation with B7 and targeted superantigen is required for MHC class II-independent T-cell proliferation but not cytotoxicity. Immunology 80: 236–241.

Lindholm et al (1993) 9301302 (patent application).

Mollick J A et al (1993) Localization of a site on bacterial superantigens that determines T cell receptor beta chain specificity. J Exp Med 177:283–93.

Newall et al (1991) In vivo T-cell activation by staphylococcal enterotoxin B prevents outgrowth of a malignant tumor. Proc Natl Acad Sci USA 88 1074–1078.

Schad E M et al (1995) Crystal structure of the superantigen, Staphylococcal enterotoxin type A. EMBO J 14:3292–301.
Stern et al (1989) WO8907947 (patent application).

Terman et al (1991) WO9110680 (patent application).
Terman et al (1993) WO9324136 (patent application).
von Heijne, G (1986). A new method for predicting signal sequence cleavage sites. Nucleic Acid Res, 14, 1483–90.

What is claimed is:

1. A method of activation of the immune system of a mammal, which method comprises:
   administering to the mammal a therapeutically effective amount of a superantigen-antibody moiety, wherein,
   said superantigen is SEE, SEQ.ID.No.8, wherein region A, amino acid residues 20–27 of SEQ ID NO:8, is modified in that at least the following amino acid residue substitutions have been made: R20G, N21T, S24G, and R27K, and wherein said antibody moiety is selected from the group consisting of an antibody, a single-chain antibody, Fab, $F(ab)_2$, and Fv.

2. The method of claim 1, wherein the antibody moiety is an antibody.

3. The method of claim 2, wherein the cysteine residues allowing for cysteine interchain linkage in the antibody have been replaced with serine residues that do not allow cysteine interchain linkage.

4. The method of claim 1, wherein the antibody moiety is Fab.

5. A method of activation of the immune system of a mammal, which method comprises:

administering to the mammal a therapeutically effective amount of a superantigen-antibody moiety, wherein, said superantigen is SEE, SEQ.ID.No.8, wherein region H, amino acid residues 200–207 of SEQ ID NO:8, is modified in that at least the following amino acid residue substitutions have been made: D220G, P206S, and D207N, and wherein said antibody moiety is selected from the group consisting of an antibody, a single-chain antibody, Fab, $F(ab)_2$, and Fv.

6. The method of claim 5, wherein the antibody moiety is an antibody.

7. The method of claim 6, wherein the cysteine residues allowing for cysteine interchain linkage in the antibody have been replaced with serine residues that do not allow cysteine interchain linkage.

8. The method of claim 5, wherein the antibody moiety is Fab.

9. A method of activation of the immune system of a mammal, which method comprises:

administering to the mammal a therapeutically effective amount of a superantigen-antibody moiety, wherein, said superantigen is SEE, SEQ.ID.No.8, wherein region A, amino acid residues 20–27 of SEQ ID NO:8, and region H, amino acid residues 200–207 of SEQ ID NO:8, are modified in that at least the following amino acid residue substitutions have been made in region A: R20G, N21T, S24G, R27K, and that at least the following amino acid residue substitutions have been made in region H: D220G, P206S, and D207N and, wherein said antibody moiety is selected from the group consisting of an antibody, a single-chain antibody, Fab, $F(ab)_2$, and Fv.

10. The method of claim 9, wherein the antibody moiety is an antibody.

11. The method of claim 10, wherein the cysteine residues allowing for cysteine interchain linkage in the antibody have been replaced with serine residues that do not allow cysteine interchain linkage.

12. The method of claim 9, wherein the antibody moiety is Fab.

* * * * *

UNITED STATES PATENT AND TRADEMARK OFFICE
CERTIFICATE OF CORRECTION

PATENT NO.     : 6,514,498 B1
DATED          : February 4, 2003
INVENTOR(S)    : Per Antonsson et al.

It is certified that error appears in the above-identified patent and that said Letters Patent is hereby corrected as shown below:

Column 6,
Line 22, should read -- Region H: D200G, P206S, D207N --

Column 31,
Line 8, should read -- residue substitutions have been made: D200G, P206S --

Column 32,
Line 12, should read -- made in region H: D200G, P206S, and D207N and, Signed and Sealed this Eighth Day of June, 2004

JON W. DUDAS
*Acting Director of the United States Patent and Trademark Office*

```
                              SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 3 amino acids
         (B) TYPE: amino acid
         (D) TOPOLOGY: linear (ii) MOLECULE TYPE: peptide (xi) SEQUENCE DESCRIPTION: SEQ ID NO:1:

Gly Gly Pro
1

(2) INFORMATION FOR SEQ ID NO:2:

(i) SEQUENCE CHARACTERISTICS:
         (A) LENGTH: 24 nucleotides
         (B) TYPE: nucleic acid
         (C) STRANDEDNESS: single
         (D) TOPOLOGY: linear (xi) SEQUENCE DESCRIPTION: SEQ ID NO:2:

CAATTTTCTT GTCCACCTTG GTGC                                            24

(2) INFORMATION FOR SEQ ID NO:3:

(i) SEQUENCE CHARACTERISTICS:
         (A) LENGTH: 35 nucleotides
         (B) TYPE: nucleic acid
         (C) STRANDEDNESS: single
         (D) TOPOLOGY: linear (ix) FEATURE:
         (D) OTHER INFORMATION:  N = Inosine (xi) SEQUENCE DESCRIPTION: SEQ ID NO:3:

ACTAGTCGAC ATGGATGGAG CTNTATCATN YTCTT                                35

(2) INFORMATION FOR SEQ ID NO:4:

(i) SEQUENCE CHARACTERISTICS:
         (A) LENGTH: 41 nucleotides
         (B) TYPE: nucleic acid
         (C) STRANDEDNESS: single
         (D) TOPOLOGY: linear (ix) FEATURE:
         (D) OTHER INFORMATION:  N = Inosine (xi) SEQUENCE DESCRIPTION: SEQ ID NO:4:

ACTAGTCGAC ATGGGCNTCA AGATGGAGTC ACAKWYYCWG G                          41

(2) INFORMATION FOR SEQ ID NO:5:

(i) SEQUENCE CHARACTERISTICS:
         (A) LENGTH: 34 nucleotides
         (B) TYPE: nucleic acid
```

(C) STRANDEDNESS: single
                    (D) TOPOLOGY: linear (xi) SEQUENCE DESCRIPTION: SEQ ID NO:5:

GCGCCGTCTA GAATTAACAC TCATTCCTGT TGAA                                    34

(2) INFORMATION FOR SEQ ID NO:6:

(i) SEQUENCE CHARACTERISTICS:
                (A) LENGTH: 107 amino acids
                (B) TYPE: amino acid
                (D) TOPOLOGY: linear (ii) MOLECULE TYPE: peptide (xi) SEQUENCE DESCRIPTION: SEQ ID NO:6:

Asp Ala Val Met Thr Gln Thr Pro Thr Phe
1               5                   10

Leu Leu Val Ser Ala Gly Asp Arg Val Thr
                15                  20

Ile Thr Cys Lys Ala Ser Gln Ser Val Ser
                25                  30

Asn Asp Val Ala Trp Tyr Gln Gln Lys Pro
                35                  40

Gly Gln Ser Pro Thr Leu Leu Ile Ser Tyr
                45                  50

Thr Ser Ser Arg Tyr Ala Gly Val Pro Asp
                55                  60

Arg Phe Ile Gly Ser Gly Tyr Gly Thr Asp
                65                  70

Phe Thr Phe Thr Ile Ser Thr Leu Gln Ala
                75                  80

Glu Asp Leu Ala Val Tyr Phe Cys Gln Gln
                85                  90

Asp Tyr Asn Ser Pro Pro Thr Phe Gly Gly
                95                  100

Gly Thr Lys Leu Glu Ile Lys
                105

(2) INFORMATION FOR SEQ ID NO:7:

(i) SEQUENCE CHARACTERISTICS:
                (A) LENGTH: 233 amino acids
                (B) TYPE: amino acid
                (D) TOPOLOGY: linear (ii) MOLECULE TYPE: peptide (xi) SEQUENCE DESCRIPTION: SEQ ID NO:7:

Ser Glu Lys Ser Glu Glu Ile Asn Glu Lys
                5                   10

Asp Leu Arg Lys Lys Ser Glu Leu Gln Gly
                15                  20

Thr Ala Leu Gly Asn Leu Lys Gln Ile Tyr
                25                  30

Tyr Tyr Asn Glu Lys Ala Lys Thr Glu Asn
                35                  40

Lys Glu Ser His Asp Gln Phe Leu Gln His
                45                  50

```
Thr Ile Leu Phe Lys Gly Phe Phe Thr Asp
                55                      60

His Ser Trp Tyr Asn Asp Leu Leu Val Asp
                65                      70

Phe Asp Ser Lys Asp Ile Val Asp Lys Tyr
                75                      80

Lys Gly Lys Lys Val Asp Leu Tyr Gly Ala
                85                      90

Tyr Tyr Gly Tyr Gln Cys Ala Gly Gly Thr
                95                     100

Pro Asn Lys Thr Ala Cys Met Tyr Gly Gly
               105                     110

Val Thr Leu His Asp Asn Asn Arg Leu Thr
               115                     120

Glu Glu Lys Lys Val Pro Ile Asn Leu Trp
               125                     130

Leu Asp Gly Lys Gln Asn Thr Val Pro Leu
               135                     140

Glu Thr Val Lys Thr Asn Lys Lys Asn Val
               145                     150

Thr Val Gln Glu Leu Asp Leu Gln Ala Arg
               155                     160

Arg Tyr Leu Gln Glu Lys Tyr Asn Leu Tyr
               165                     170

Asn Ser Asp Val Phe Asp Gly Lys Val Gln
               175                     180

Arg Gly Leu Ile Val Phe His Thr Ser Thr
               185                     190

Glu Pro Ser Val Asn Tyr Asp Leu Phe Gly
               195                     200

Ala Gln Gly Gln Tyr Ser Asn Thr Leu Leu
               205                     210

Arg Ile Tyr Arg Asp Asn Lys Thr Ile Asn
               215                     220

Ser Glu Asn Met His Ile Asp Ile Tyr Leu
               225                     230

Tyr Thr Ser
           233

(2) INFORMATION FOR SEQ ID NO:8:

(i) SEQUENCE CHARACTERISTICS:
        (A) LENGTH: 233 amino acids
        (B) TYPE: amino acid
        (D) TOPOLOGY: linear (ii) MOLECULE TYPE: peptide (xi) SEQUENCE DESCRIPTION: SEQ ID NO:8:

Ser Glu Lys Ser Glu Glu Ile Asn Glu Lys
                 5                      10

Asp Leu Arg Lys Lys Ser Glu Leu Gln Arg
                15                      20

Asn Ala Leu Ser Asn Leu Arg Gln Ile Tyr
                25                      30

Tyr Tyr Asn Glu Lys Ala Ile Thr Glu Asn
```

```
                        35                          40
Lys Glu Ser Asp Asp Gln Phe Leu Glu Asn
                        45                          50
Thr Leu Leu Phe Lys Gly Phe Phe Thr Gly
                        55                          60
His Pro Trp Tyr Asn Asp Leu Leu Val Asp
                        65                          70
Leu Gly Ser Lys Asp Ala Thr Asn Lys Tyr
                        75                          80
Lys Gly Lys Lys Val Asp Leu Tyr Gly Ala
                        85                          90
Tyr Tyr Gly Tyr Gln Cys Ala Gly Gly Thr
                        95                         100
Pro Asn Lys Thr Ala Cys Met Tyr Gly Gly
                       105                         110
Val Thr Leu His Asp Asn Asn Arg Leu Thr
                       115                         120
Glu Glu Lys Lys Val Pro Ile Asn Leu Trp
                       125                         130
Ile Asp Gly Lys Gln Thr Thr Val Pro Ile
                       135                         140
Asp Lys Val Lys Thr Ser Lys Lys Glu Val
                       145                         150
Thr Val Gln Glu Leu Asp Leu Gln Ala Arg
                       155                         160
His Tyr Leu His Gly Lys Phe Gly Leu Tyr
                       165                         170
Asn Ser Asp Ser Phe Gly Gly Lys Val Gln
                       175                         180
Arg Gly Leu Ile Val Phe His Ser Ser Glu
                       185                         190
Gly Ser Thr Val Ser Tyr Asp Leu Phe Asp
                       195                         200
Ala Gln Gly Gln Tyr Pro Asp Thr Leu Leu
                       205                         210
Arg Ile Tyr Arg Asp Asn Lys Thr Ile Asn
                       215                         220
Ser Glu Asn Leu His Ile Asp Leu Tyr Leu
                       225                         230
Tyr Thr Thr (2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:9:

Gly Thr Ala Leu Gly Asn Leu Lys
                 5

(2) INFORMATION FOR SEQ ID NO:10:
```

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:  10:

Arg  Asn  Ala  Leu  Ser  Asn  Leu  Arg
                    5

(2) INFORMATION FOR SEQ ID NO:11:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:  11:

Lys  Thr  Glu  Asn  Lys  Glu  Ser  His  Asp  Gln
                    5                        10

Phe  Leu  Gln  His (2) INFORMATION FOR SEQ ID NO:12:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:  12:

Ile  Thr  Glu  Asn  Lys  Glu  Ser  Asp  Asp  Gln
                    5                        10

Phe  Leu  Glu  Asn (2) INFORMATION FOR SEQ ID NO:13:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (xi) SEQUENCE DESCRIPTION: SEQ ID NO:  13:

Asp  His  Ser (2) INFORMATION FOR SEQ ID NO:14:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (xi) SEQUENCE DESCRIPTION: SEQ ID NO:  14:

Gly  His  Pro (2) INFORMATION FOR SEQ ID NO:15:

(i) SEQUENCE CHARACTERISTICS:
            (A) LENGTH: 8 amino acids

```
            (B) TYPE: amino acid
            (D) TOPOLOGY: linear (ii) MOLECULE TYPE: peptide (xi) SEQUENCE DESCRIPTION: SEQ ID NO:  15:

Phe  Asp  Ser  Lys  Asp  Ile  Val  Asp
                    5

(2) INFORMATION FOR SEQ ID NO:16:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:  16:

Leu  Gly  Ser  Lys  Asp  Ala  Thr  Asn
                    5

(2) INFORMATION FOR SEQ ID NO:17:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:  17:

Asn  Thr  Val  Pro  Leu  Glu  Thr  Val  Lys  Thr
                    5                        10
Asn  Lys  Lys  Asn (2) INFORMATION FOR SEQ ID NO:18:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:  18:

Thr  Thr  Val  Pro  Ile  Asp  Lys  Val  Lys  Thr
                    5                        10
Ser  Lys  Lys  Glu (2) INFORMATION FOR SEQ ID NO:19:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:  19:

Arg  Tyr  Leu  Gln  Glu  Lys  Tyr  Asn  Leu  Tyr
                    5                        10
Asn  Ser  Asp  Val  Phe  Asp
                    15

(2) INFORMATION FOR SEQ ID NO:20:
```

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO: 20:

His Tyr Leu His Gly Lys Phe Gly Leu Tyr
                 5                   10
Asn Ser Asp Ser Phe Gly
                 15

(2) INFORMATION FOR SEQ ID NO:21:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 21:

Thr Ser Thr Glu Pro Ser Val Asn
                 5

(2) INFORMATION FOR SEQ ID NO:22:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 22:

Ser Ser Glu Gly Ser Thr Val Ser
                 5

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 23:

Gly Ala Gln Gly Gln Tyr Ser Asn
                 5

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 24:

Asp Ala Gln Gly Gln Tyr Pro Asp
                 5